US005821070A

United States Patent [19]

Lee et al.

[11] Patent Number: 5,821,070
[45] Date of Patent: Oct. 13, 1998

[54] ANTIBODIES REACTIVE WITH RETINOBLASTOMA BINDING PROTEINS AND METHODS OF USING SAME

[75] Inventors: Wen-Hwa Lee; Bei Shan, both of San Antonio, Tex.

[73] Assignee: Board of Regents of the University of Texas System, Austin, Tex.

[21] Appl. No.: 139,937

[22] Filed: Oct. 20, 1993

Related U.S. Application Data

[62] Division of Ser. No. 979,156, Nov. 20, 1992.
[51] Int. Cl.$^6$ ....................... G01N 33/574; G01N 33/53; C07K 16/30; C12N 5/12
[52] U.S. Cl. ..................... 435/7.23; 435/7.2; 435/325; 435/330; 530/287.1; 530/387.7; 530/388.8; 530/391.3
[58] Field of Search .............................. 530/387.1, 388.8, 530/388.85, 389.1, 389.7, 388.3, 387.7, 391.3; 435/240.27, 7.2, 7.23, 325, 330

[56] References Cited

U.S. PATENT DOCUMENTS 4,942,123  7/1990  Lee et al. ..................... 435/6

FOREIGN PATENT DOCUMENTS

| 0 259 031 A2 | 3/1988 | European Pat. Off. . |
| 0 293 266 A2 | 11/1988 | European Pat. Off. . |
| PCT/US93/11310 | 11/1993 | WIPO . |

OTHER PUBLICATIONS

Char, DH et al., Retina, 3(3):200–5, 1983.
Sevier,ED et al, Clin. Chem., 27(11):1797–1806, 1981.
Ali et al., "Retinoblastoma Gene Product–Associated Proteins in Human Colan Cancer Cell Lines"; *Biochem. and Biophys. Res. Comm.* 194(2): 848–854 (1993).
Bandara et al., "Cyclin A and the Retinoblastoma Gene Product Complex with a Common Transcription Factor"; *Nature* 352: 249–251 (1991).
Helin et al., "A cDNA Encoding a pRB–Binding Protein with Properties of the Transcription Factor E2F"; *Cell* 70: 337–350 (1992).
Defeo–Jones et al., "Cloning of cDNA's for Celllular Proteins that Bind to the Retinoblastoma Gene Product"; *Nature* 352: 251–254 (1991).
Kaelin, Jr. et al., "Identification of Cellular Proteins tha can Interact Specifically with the T/E1A–Binding Region of the Retinblastoma Gene Product"; *Cell* 64: 521–532 (1991).
Kaelin, Jr. et al., "Expression Cloning of a cDNA Encoding a Retinblastoma–Binding Protein with E2F–like Properties"; *Cell* 70: 351–364 (1992).
Nevins, J.R., "E2F: A Link Between the Rb Tumor Suppressor Protein and Viral Oncoproteins"; *Science* 258: 427–428 (1992).
Ray et al., "Identification of a 60–Kilodalton Rb–Binding Protein, RBP60, That Allows the Rb–E2F Complex to Bind DNA"; *Mol. and Cell. Biology* 12(10): 4327–4333 (1992).

Huang, Shi et al., Nature, 350: 160–162, 14 Mar. 1991.
Sevier, E.D. et al, Clin. Chem, 27(11):1797–1806, 1981.
Defeo–Jones, et al, Nature, 352:251–254, 18 Jul. 1991.
Austin, C.A. et al, FEBS LETTERS, 266(1,2):115–117, Jun. 1990.
Fung et al., "Function of the Human Retinoblastome Gene" in *Recessive Oncogenes and Tumor Suppression*, Cavenee, Hastie and Stanbridge, Eds., Cold Spring Harbor Laboratory Press, New York, pp. 117–123 (1989).
Cooper, G.M., in *Oncogenes*, Jones and Bartlett Publishers, Boston, Mass., pp. 121–139 (1990).
Marx, J.L., "Eye Cancer Gene Linked to New Malignancies" *Science* 241:293–294 (1988).
Lee et al., "Inactivation of the Retinoblastoma Susceptibility Gene in Human Breast Cancers" *Science* 241:218–221 (1988).
Yokota et al., "Altered expression of the retinoblastoma (RB) gene in small cell carcinoma of the lung" *Oncogene* 3:471–475 (1988).
Dryja et al., "Genetic Sequences That Predispose to Retinoblastoma and Osteosarcoma" Symposium on Fundamental Cancer Research by The University of Texas System Cancer Center, vol. 39, pp. 115–119 (1987).
Horowitz et al., "Frequent inactivation of the retinoblastoma anti–oncogene is restricted to a subset of human tumor cells" *PNAS USA* 87:2775–2779 (1990).
Fung et al., "Structural Evidence for the Authenticity of the Human Retinoblastoma Gene" *Science* 236:1657–1661 (1987).
Cavenee et al., "Expression of recessive alleles by chromosomal mechanisms in retinoblastoma" *Nature* 305:779–784 (1983).
Lalande et al., "Molecular Detection and Differentiation of Deletions in Band 13q14 in Human Retinoblastoma" *Cancer Genet. Cytogenet.* 23:151–157 (1986).
Lee et al., "Human Retinoblastoma Susceptibility Gene: Cloning, Identification, and Sequence" *Science* 235:1394–1399 (1987).
Kolata, G., "Human Cancer Gene Sequenced" *Science*, p. 1323 (13 Mar. 1987).
DeCaprio et al., "SV40 Large Tumor Antigen Forms a Specific Complex with the Product of the Retinoblastoma Susceptibilty Gene" *Cell* 54:275–283 (1988).

(List continued on next page.)

*Primary Examiner*—Susan A. Loring
*Attorney, Agent, or Firm*—Townsend & Townsend & Crew LLP

[57] ABSTRACT

This invention provides novel antibodies specifically reactive with a nuclear retinoblastoma-associated polypeptide, wherein the polypeptide specifically binds to the protein product of the retinoblastoma gene. Also provided by this invention are antibodies specifically reactive with proteins having E2F biological activity. Methods of using these antibodies also are claimed.

16 Claims, 16 Drawing Sheets

OTHER PUBLICATIONS

Dyson et al., "The Human Papilloma Virus–16 E7 Oncoprotein Is Able to Bind to the Retinoblastoma Gene Product" *Science* 243:934–937 (1989).

Dryja et al., "Chromosome 13 Homozygosity in Osteosarcoma without Retinoblastoma" *Am. J. Hum. Genet.* 38:59–66 (1986).

Rapaport et al., "Detection of homozygous deletion of 13q14 in retinoblastomas" *Invest. Ophthalmol. & Visual Sci.* 27 (3) :194 (1986).

Bagchi et al., *Cell* 65:1063–1072 (1991).

Bookstein et al., *Proc. Natl. Acad. Sci. USA* 87:7762–7766 (1990).

Bookstein et al., *Science* 247:712–715 (1990).

Buchkovich et al., *Cell* 58:1097–1105 (1989).

Chen et al., *Cell Growth & Differentiation* 3:119–125 (1992).

Chen et al., *Cell* 58:1193–1198 (1989).

DeCaprio et al., *Cell* 58:1085–1095 (1989).

Fields et al., *Science* 249:1046–1049 (1990).

Fields et al., *Nature* 340:245–246 (1989).

Friend et al., *Nature* 323:643–646 (1986).

Goodrich et al., *Cancer Research* 52:1968–1973 (1992).

Hiebert et al., *Proc. Natl. Acad. Sci. USA* 86:3594–3598 (1989).

Horowitz et al., *Science* 243:937–940 (1989).

Hu et al., *The EMBO Journal* 9(4):1147–1155 (1990).

Huang et al., *Science* 242:1563–1566 (1988).

Huang et al., *The EMBO Journal* 9(6):1815–1822 (1990).

Keyomarsi et al., *Cancer Research* 51:3602–3609 (1991).

Lees et al., *The EMBO Journal* 10(13):4279–4290 (1991).

Lin et al., *The EMBO Journal* 10(4) :857–864 (1991).

Mudryj et al., *Cell* 65:1243–1253 (1991).

Mudryj et al., *The EMBO Journal* 9(7) :2179–2184 (1990).

Neill et al., *Journal of Virology* 65(10):5364–5373 (1991).

Shew et al., *Proc. Natl. Acad. Sci. USA* 87:6–10 (1990).

Shirodkar et al., *Cell* 68:157–166 (1992).

Sumegi et al., *Cell Growth & Differentiation* 247–250 (1990).

Takahashi et al., *Proc. Natl. Acad. Sci. USA* 88:5257–5261 (1991).

Wang et al., *Cell Growth & Differentiation* 233–239.

Wang et al., *Cell Growth & Differentiation* 1:429–437 (1990).

Whyte et al., *Nature* 334:124–129 (1988).

Lee et al., "The retinoblastoma susceptibility gene encodes a nuclear phosphoprotein associated with DNA binding activity" *Nature* 329:642–645 (1987).

FIG. 4B

KbAp2p

```
         10        20        30        40        50        60        70        80
CGCCTTGACCTTGCTGGGAATGCTCGGTCAGACAAGGGCAGCATGTCTGAAGACTGTGGGCCAGGAACCTCCGGGGAGCT 80
GGGCGGCTGAGGCGATCAAAATTGAGCCAGAGGATCTGGACATCATTCAGGTCACCGTCCCAGACCCCTCGCCAACCTCT 160
GAGGAAATGACAGACTCG 178
```

RbAp2r

```
         10        20        30        40        50        60        70        80
TTTTTTACTTATTTAAAAAGGCCTTGGTGGCAGGAATATAGTGTAAAAATCATTGGAAAAACTAAAAGGCATCGATACAT 80
ATCCGAATATACATTTTGTACATAAATTACATTTCCTTTAGTCTTTCTGAGTGAGGTCCTGATTCAGTACT 151
```

FIG. 10

RbAp8p

```
         10        20        30        40        50        60        70        80
TTTACGACAGAGCACTATTGCCAAGCGTTCAAATGCAGCACCATTAAGTAACACAAAAAAAGCATCTGGGAAGACTGTAT 80
CTACTGCTAAAGCAGGAGTGAAACAACCAGAAAGGAGTCAGGTTAAAGAAGAAGTATGTATGTCACTGAAACCTGAGTAC 160
CATAAGGAGAATAGAAGGTGCAGCCGAAATAGCGGACAAATTGAAGTGGATACCTGAAGTATCAGTGTCTTCAAGTCATT 240
CTTCAGTGTCATCTT 255
```

RbAp8r

```
         10        20        30        40        50        60        70        80
GAATTCAACTGTAGCTTGGTTTTCCAAAGTATCTGGATCTAGTATTTCAGTCTTTTTGTCTTCTTCAGCACAACATTTTA 80
CACAGACATATTCTTTGTCTTCCTCGCCCATCTGCTGTGCTTGAGAAAGACTTAACCCAACACAATCACCATGAAACCAG 160
TCATCACATCTCCACAGCCAACCATAACTGTTGCATGTGTTTTTGCAAACCACACTGTTGCTGGAGTCACATATATTCGT 240
TCAAT 245
```

FIG. 11

RbAp15p

```
         10        20        30        40        50        60        70        80
GAATTCAGTGGAGCACCAGTAGAAGGTGCAGGAGAAGAGGCATTGACTCCATCAGTTCCTATAAATAAAGGTCCCAAACC 80
TAAGAGGGAGAAGAAGGAGCCTGGTACCAGAGTGAGAAAAACACCTACATCATCTGGTAAACCTAGTGCAAAGAAAGTGA 160
AGAAACGGAATCCTTGGTCAGATGATGAATCCAAGTCAGAAAGTGATTTGGAAGAAACAGAACCTGTGGTTATTCCAAGA 240
GATTCTTTGCTTAGGAGAGCAGCAGCCGAAAGACCTAAATACACATTTAATTTCTCAGAAGAAGAGGATGATGATGCTGA 320
TGATGATGATGACAATAATGATTTAGAGGAATTGAAAGTTAAAGCATCTCCCATAACAAATGATGGGGAAGATGAAT 400
         410       420       430       440       450       460       470       480
TTGTTCCTTCAGATGGGTTAGATAAAGATGAATATACATTTTCACCAGGCAAATCAAAAGCCTCACCAGAAAAATCTTTG 480
CATGACAAAAAAAGTCAGGATTTTGGAAATCTCTTCTCATTTCCTTCATATTCTCAGAAGTCAGAAGATGATTCAGCTAA 560
ATTTGACAGTAATGAAGAAGATTCTGCTTCTGTTTTTTCACCATCATTTGGTCTGAAACAGACAGATAAAGTTCCAAGTA 640
AAACGGTAGCTGCTAAAAAGGGAAAACCGTCTTCAGATACAGTCCCTA 688
```

RbAp15r

```
         10        20        30        40        50        60        70        80
GCAATGTTTAATTAAGTGGGGAAAGAGCACAAACATTTTTCAACAAATACTTGTGTTGTCCTTTTGTCTTCTCTGTCTCA 80
GACCTTTTGTACATCTGGCTTATTTTAATGTGATGATGTAATTGACCGTTTTTTATTATTGTGGGTAGGCCTTTTAACATT 160
TTGTTCTTACACATACAGTTTTATGCTCTTTTTTACTCATTGAAATGTCACGTACTGTCTGATTGGCTTGTAGAATTGGT 240
TATAGACTGCCGTGCATTAGCACAGATTTTAATTGTCATGGTTACAAACTACAGACCTGCTTTTTGAAATGAAATTTAAA 320
CATTAAAAATGGAACTGTGAAAAAAAAA 348
```

FIG. 12

RbAp4

```
         10        20        30        40        50        60        70        80
GAATTCCGGGCCAAGAAGCCTAATGAGAAAAACAAACCACTTGATAATAAGGGAGAAAAAAGAAAAAGAAAAACTGAAGA  80
AAAAGGCGTAGATAAAGATTTTGAGTCTTCTTCAATGAAAATCTCGAAACTAGAAGTGACTGAAATAGTGAAACCATCAC 160
CAAAGCGCAAAATGGAACCTGATACTGAAAAAATGGATAGGACCCCTGAAAAGGACAAAATTTCTTTAAGTGCGCCAGCC 240
AAAAAAATCAAACTCAACAGAGAAACTGGGAAGAAAATTGGAAGTACAGAAAATATATCAAACACAAAAGAACCCTCTGA 320
AAAATTGGAGTCAACATCTAGCAAAGTTAAACAAGAAAAAGTCAAAGGAAAGGTCAGACGAAAAGTGACTGGAACTGAAG 400
        410       420       430       440       450       460       470       480
GATCCAGCTCAACTCTGGTGGATTACaCCaGTACGAGCTCAACTGGAGGCAGTCCTGTGCGGAAATCTGAAGAAAAAACA 480
GATACAAAGCGAACTGTGATTAAAACGATGGAAGAATATAATAATGACAATACCGCGCCACGTGAAGATGTTATCATTAT 560
GATTCAGGTTCCTCAATCCAAATGGGATAAAGATGACTTTGAATCTGAAGAAGAAGATGTTAAATCCACACAGCCTATAT 640
CAAGTGTAGGAAAACCTGCTAGTGTTATAAAAAATGTTAGTACAAAGCCATCAAATATAGTCAAGTATCCTGAGAAAGAA 720
AGTGAGCCATCCGAGAAAATTCAGAAATTCACCAAGGACGTGAGCCATGAAATCATACAACATGAGGTTAAAAGTTCAAA 800
        810       820       830       840       850       860       870       880
AAACTCTGCATCTAGTGAAAAAGGGAAAACCAAAGATCGAGATTATTCAGTGTTGGAAAAGGAGAACCCTGAAAAGAGGA 880
AGAACAGCACTCAGCCAGAGAAAGAGAGTAATTTTGGACCGTCTGAATGAACAAGGAAATTTTAAAAGTCTGTCTCAATCT 960
TCCAAAGAGGCTAGAACGTCAGATAAACATGATTCCACTCGTGCTTCCTCAAATAAAGACTTCACTCCCAATAGAGACAA 1040
AAAAACTGACTATGACACCAGAGAGTATTCAAGTTCCAAAcgTAGAGATGAAAAGAATGAATTAACAAGACGAAAAGACT 1120
CTCCTTCTCGGAATAAAGATTCTGCATCTGGACAGAAAAATAAACCAAGGGAAGAGAGAGATTTGCCTAAAAAAGGAACA 1200
       1210      1220      1230      1240      1250      1260      1270      1280
GGAGATTCCAAAAAAAGTAATTCTAGTCCCTCAAGAGACAGAAAACCTCATGATCACAAAGCCACTTATGATACTAAACG 1280
GCCAAATGAAGAGACAAAATCTGTAGATAAAAATCCTTGTAAGGATCGTGAGAAGCATGTATTAGAAGCAAGGAACAATA 1360
AAGAGTCAAGTGGCAATAAAcTaCTTTTATATACTTAACCCACCAGAGAcAcAGGTTGAAAAAGAGCAAATTACTGGGCAA 1440
ATTGACAAGAGTACTGTCAAGCCTAAACCCCAGTTAAGTCATTCCTCTAGACTTTCCTCTGACTTAACTAGAGAAACTCA 1520
TGAAGCTGCTTTTTGAACCAGACTATAATGAAAGTGACAGTGAAAGTAATGTTTCTGTAAAAGAAGAGGAATCTTCAGGAA 1600
       1610      1620      1630      1640      1650      1660      1670      1680
ACATTTCTAAGGACCTGAAAGATAAAATAGTGGAGAAAGCAAAAGAGAGCCTGGACACAGCAGCAGTTGTCCAGGTGGGC 1680
ATAAGCAGGAATCAGAGCCACAGCAGCCCCAGCGTCAGCCCCAGCAGAAGCCACAGTCCTTCTGGAAGCCAGACCCGAAG 1760
CCACAGTAGCAGTGCCAGCTCAGCAGAAAGTCAGGACAGC                                         1800
```

FIG. 13

RbAp I O

```
           10        20        30        40        50        60        70        80
         ....|....|....|....|....|....|....|....|....|....|....|....|....|....|....|....|
GAATTCCGGCCGGAATTAATTCCGGGGATTTCCTGGGGAATCAGGAAGATATCCATAATCTTCAACTGCGGGTAAAAGAG   80
ACATCAAATGAGAATTTGAGATTACTTCATGTGATAGAGGACCGTGACAGAAAAGTTGAAAGTTTGCTAAATGAAATGAA  160
AGAATTAGACTCAAAACTCCATTTACAGGAGGTACAACTAATGACCAAAATTGAAGCATGCATAGAATTGGAAAAAATAG  240
TTGGGGAACTTAAGAAAGAAAACTCAGATTTAAGTGAAAAATTGGAATATTTTTCTTGTGATCACCAGGAGTTACTCCAG  320
AGAGTAGAAACTTCTGAAGGCCTCAATTCTGATTTAGAAATGCATGCAGATAAATCATCACGTGAAGATATTGGAGATAA  400
          410       420       430       440       450       460       470       480
         ....|....|....|....|....|....|....|....|....|....|....|....|....|....|....|....|
TGTGGCCAAGGTGAATGACAGCTGGAAGGAGAGATTTCTTGATGTGGAAAATGAGCTGAGTAGGATCAGATCGGAGAAAG  480
CTAGCATTGAGCATGAAGCCCTCTACCTGGAGGCTGACTTAGAGGTAGTTCAAACAGAGAAGCTATGTTTAGAAAAAGAC  560
AATGAAAATAAGCAGAAGGTTATTGTCTGCCTTGAAGAAGAACTCTCAGTGGTCACAAGTGAGAGAAACCAGCTTCGTGG  640
AGAATTAGATACTATGTCAAAAAAAACCACGGCACTGGATCAGTTGTCTGAAAAAATGAAGGAGAAAACACAAGAGCTTG  720
AGTCTCATCAAAGTGAGTGTCTCCATTGCATTCAGGTGGCAGAGGCAGAGGTGAAGGAAAAGACGGAACTCCTTCAGACT  800
          810       820       830       840       850       860       870       880
         ....|....|....|....|....|....|....|....|....|....|....|....|....|....|....|....|
TTGTCCTCTGATGTGAGTGAGCTGTTAAAAGACAAAACTCATCTCCAGGAAAAGCTGCAGAGTTTGGAAAAGGACTCACA  880
GGCACTGTCTTTGACAAAATGTGAGCTGGAAAACCAAATTGCACAACTGAATAAAGAGAAAGAATTGCTTGTCAAGGAAT  960
CTGAAAGCCTGCAGGCCAGACTGAGTGAATCAGATTATGAAAAGCTGAATGTCTCCAAGGCCTTGGAGGCCGCACTGGTG 1040
GAGAAAGGTGAGTTCGCATTGAGGCTGAGCTCAACACAGGAGGAAGTGCATCAGCTGAGAAGAGGCATCGAGAAACTGAG 1120
AGTTCGCATTGAGGCCGATGAAAAGAAGCAGCTGCACATCGCAGAGAAACTGAAAGAACGCGAGCGGGAGAATGATTCAC 1200
         1210      1220      1230      1240      1250      1260      1270      1280
         ....|....|....|....|....|....|....|....|....|....|....|....|....|....|....|....|
TTAAGGATAAAGTTGAGAACCTTGAAAGGGAATTGCAGATGTCAGAAGAAAACCAGGAGCTAGTGATTCTTGATGCCGAG 1280
AATTCCAAAGCAGAAGTAGAGACTCTAAAAACACAAATAGAAGAGATGGCCAGAAGCCTGAAAGTTTTTGAATTAGACCT 1360
TGTCACGTTAAGGTCTGAAAAAGAAAATCTGACAAAACAAATACAAGAAAAACAAGGTCAGTTGTCAGAACTAGACAAGT 1440
TACTCTCTTCATTTAAAAGTCTGTTAGAAGAAAAGGAGCAAGCAGAGATACAGATCAAAGAAGAATCTAAAACTGCAGTG 1520
GAGATGCTTCAGAATCAGTTAAAGGAGCTAAATGAGGCAGTAGCAGCCTTGTGTGGTGACCAAGAAATTATGAAGGCCAC 1600
         1610      1620      1630      1640      1650      1660      1670      1680
         ....|....|....|....|....|....|....|....|....|....|....|....|....|....|....|....|
AGAACAGAGTCTAGACCCACCAATAGAGGAAGAGCATCAGCTGAGAAATAGCATTGAAAAGCTGAGAGCCCGCCTAGAAG 1680
CTGATGAAAAGAAGCAGCTCTGTGTCTTACAACAACTGAAGGAAAGTGAGCATCATGCAGATTTACTTAAGGGTAGAGTG 1760
GAGAACCTTGAAAGAGAGCTAGAGATAGCCAGGACAAACCAAGAGCATGCAGCTCTTGAGGCAGAGAATTCCAAAGGAGA 1840
GGTAGAGACCCTAAAAGCAAAAATAGAAGGGATGACCCAAAGTCTGAGAGGTCTGGAATTAGATGTTGTTACTATAAGGT 1920
CAGAAAAAGAAAATCTGACAAATGAATTACAAAAAGAGCAAGAGCGAATATCTGAATTAGAAATAATAAATTCATCATTT 2000
         2010      2020      2030      2040      2050      2060      2070      2080
         ....|....|....|....|....|....|....|....|....|....|....|....|....|....|....|....|
GAAAATATTTTGCAAGAAAAAGAGCAAGAGAAAGTACAGATGAAAGAAAAATCAAGCACTGCCATGGAGATGCTTCAAAC 2080
ACAATTAAAAGAGCTCAATGAGAGAGTGGCAGCCCTGCATAATGACCAAGAAGCCTGTAAGGCCAAAGAGCAGAATCTTA 2160
GTAGTCAAGTAGAGTGTCTTGAACTTGAGAAGGCTCAGTTGCTACAAGGCCTTGATGAGGCCAAAAATAATTATATTGTT 2240
TTGCAATCTTCAGTGAATGGCCTCATTCAAGAAGTAGAAGATGGCAAGCAGAAACTGGAGAAGAAGGATGAAGAAATCAG 2320
TAGACTGAAAAATCAAATTCAAGACCAAGAGCAGCTTGTCTCTAAACTGTCCCAGGTGGAAGGAGAGCACCAACTTTGGA 2400
         2410      2420      2430      2440      2450      2460      2470      2480
         ....|....|....|....|....|....|....|....|....|....|....|....|....|....|....|....|
AGGAGCAAAACTTAGAACTGAGAAATCTGACAGTGGAATTGGAGCAGAAGATCCAAGTGCTACAATCCAAAAATGCCTCT 2480
TTGCAGGACACATTAGAAGTGCTGCAGAGTTCTTACAAGAATCTAGAGAATGAGCTTGAATTGACAAAAATGGACAAAAT 2560
GTCCTTTGTTGAAAAAGTAAACAAAATGACTGCAAAGGAAACTGAGCTGCAGAGGGAAATGCATGAGATGGCACAGAAAA 2640
CAGCAGAGCTGCAAGAAGAACTCAGTGGAGAGAAAAATAGGCTAGCTGGAGAGTTGCAGTTACTGTTGGAAGAAATAAAG 2720
AGCAGCAAAGATCAATTGAAGGAGCTCACACTAGAAAATAGTGAATTGAAGAAGAGCCTAGATTGCATGCACAAAGACCA 2800
```

Figure 14 (Page 1 of 2)

RbAp10 CONT.

```
         2810      2820      2830      2840      2850      2860      2870      2880
GGTGGAAAAGGAAGGGAAAGTGAGAGAGGAAATAGCTGAATATCAGCTACGGCTTCATGAAGCTGAAAAGAAACACCAGG 2880
CTTTGCTTTTGGACACAAACAAACAGTATGAAGTAGAAATCCAGACATACCGAGAGAAATTGACTTCTAAAGAAGAATGT 2960
CTCAGTTCACAGAAGCTGGAGATAGACCTTTTAAAGTCTAGTAAAGAAGAGCTCAATAATTCATTGAAAGCTACTACTCA 3040
GATTTTGGAAGAATTGAAGAAAACCAAGATGGACAATCTAAAATATGTAAATCAGTTGAAGAAGGAAAATGAACGTGCCC 3120
AGGGGAAAATGAAGTTGTTGATCAAATCCTGTAAACAGCTGGAAGAGGAAAAGGAGATACTGCAGAAAGAACTCTCTCAA 3200
         3210      3220      3230      3240      3250      3260      3270      3280
CTTCAAGCTGCACAGGAGAAGCAGAAAACAGGTACTGTTATGGATACCAAGGTCGATGAATTAACAACTGAGATCAAAGA 3280
ACTGAAAGAAACTCTTGAAGAAAAAACCAAGGAGGCAGATGAATACTTGGATAAGTACTGTTCCTTGCTTATAAGCCATG 3360
AAAAGTTAGAGAAAGCTAAAGAGATGTTAGAGACACAAGTGGCCCATCTGTGTTCACAGCAATCTAAACAAGATTCCCGA 3440
GGGTCTCCTTTGCTAGGTCCAGTTGTTCCAGGACCATCTCCAATCCCTTCTGTTACTGAAAAGAGGTTATCATCTGGCCA 3520
AAATAAAGCTTCAGGCAAGAGGCAAAGATCCAGTGGAATATGGGAGAATGGTGGAGGACCAACACCTGCTACCCCAGAGA 3600
         3610      3620      3630      3640      3650      3660      3670      3680
GCTTTTCTAAAAAAAGCAAGAAAGCAGTCATGAGTGGTATTCACCCTGCAGAAGACACGGAAGGTACTGAGTTTGAGCCA 3680
GAGGGACTTCCAGAAGTTGTAAAGAAAGGGTTTGCTGACATCCCGACAGGAAAGACTAGCCCATATATCCTGCGAAGAAC 3760
AACCATGGCAACTCGGACCAGCCCCCGCCTGGCTGCACAGAAGTTAGCGCTATCCCCACTGAGTCTCGGCAAAGAAAATC 3840
TTGCAGAGTCCTCCAAACCAACAGCTGGTGGCAGCAGATCACAAAAGGTCAAAGTTGCTCAGCGGAGCCCAGTAGATTCA 3920
GGCACCATCCTCCGAGAACCCACCACGAAATCCGTCCCAGTCAATAATCTTCCTGAGAGAAGTCCGACTGACAGCCCCAG 4000
         4010      4020      4030      4040      4050      4060      4070      4080
AGAGGGCCTGAGGGTCAAGCGCCGGCGACTTGTCCCCAGCCCCAAAGCTGGACTGGAGTCCAAGGGCAGTGAGAACTGTA 4080
AGGTCCAGTGAAGGCACTTTGTGTGTCAGTACCCCTGGGAGGTGCCAGTCATTGAATAGATAAGGCTGTGCCTACAGGAC 4160
TTCTCTTTAGTCAGGGCATGCTTTATTAGTGAGGAGAAAACAATTCCTTAGAAGTCTTAAATATATTGTACTCTTTAGAT 4240
CTCCCATGTGTAGGTATTGAAAAAGTTTGGAAGCACTGATCACCTGTTAGCATTGCCATTCCTCTACTGCAATGTAAATA 4320
GTATAAAGCTATGTATATAAAGCTTTTTGGTAATATGTTACAATTAAAATGACAAGCACTATATCACAATCTCTGTTTGT 4400
         4410      4420      4430      4440      4450      4460      4470      4480
ATGTGGGTTTTACACTAAAAAAAATGCAAAACACATTTTATTCTTCTAATTAACAGCTCCTAGGAAAATGTAGACTTTTGC 4480
TTTATGATATTCTATCTGTAGTATGAGGCATGGAATAGTTTTGTATCGGGAATTTCTCAGAGCTGAGTAAAATGAAGGAA 4560
AAGCATGTTATGTGTTTTTAAGGAAAATGTGCACACATATACATGTAGGAGTGTTTATCTTTCTCTTACAATCTGTTTTA 4640
GACATCTTTGCTTATGAAACCTGTACATATGTGTGTGTGGGTATGTGTTTATTTCCAGTGAGGGCTGCAGGCTTCCTAGA 4720
GGTGTGCTATACCATGCGTCTGTCGTTGTGCTTTTTTCTGTTTTTAGACCAATTTTTTACAGTTCTTTGGTAAGCATTGT 4800
         4810      4820      4830      4840      4850      4860      4870      4880
CGTATCTGGTGATGGATTAACATATAGCCTTTGTTTTCTAATAAAATAGTCGCCTTCGTAAAAAAAAA 4868
```

Figure 14 (Page 2 of 2)

5,821,070

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Leu  Xaa  Ser  Xaa  Glu  Asp  Asp  Glu
1                   5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

Ser  Pro  Gly  Lys
1

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TTTCGCGCGC GCGAAA　　　　　　　　　　　　　　　　　　　　　　　　　　　　16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTTAGCGCGC GCTAAA　　　　　　　　　　　　　　　　　　　　　　　　　　　　16

( 2 ) INFORMATION FOR SEQ ID NO:5:

( i ) SEQUENCE CHARACTERISTICS:
        ( A ) LENGTH: 178 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CGCCTTGACC TTGCTGGGAA TGCTCGGTCA GACAAGGGCA GCATGTCTGA AGACTGTGGG　　60

CCAGGAACCT CCGGGGAGCT GGGCGGCTGA GGCGATCAAA ATTGAGCCAG AGGATCTGGA　　120

CATCATTCAG GTCACCGTCC CAGACCCCTC GCCAACCTCT GAGGAAATGA CAGACTCG　　178

( 2 ) INFORMATION FOR SEQ ID NO:6:

( i ) SEQUENCE CHARACTERISTICS:
        ( A ) LENGTH: 151 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| TTTTTTACTT | ATTTAAAAAG | GCCTTGGTGG | CAGGAATATA | GTGTAAAAAT | CATTGGAAAA | 60 |
| ACTAAAAGGC | ATCGATACAT | ATCCGAATAT | ACATTTTGTA | CATAAATTAC | ATTTCCTTTA | 120 |
| GTCTTTCTGA | GTGAGGTCCT | GATTCAGTAC | T | | | 151 |

( 2 ) INFORMATION FOR SEQ ID NO:7:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| TTTACGACAG | AGCACTATTG | CCAAGCGTTC | AAATGCAGCA | CCATTAAGTA | ACACAAAAAA | 60 |
| AGCATCTGGG | AAGACTGTAT | CTACTGCTAA | AGCAGGAGTG | AAACAACCAG | AAAGGAGTCA | 120 |
| GGTTAAAGAA | GAAGTATGTA | TGTCACTGAA | ACCTGAGTAC | CATAAGGAGA | ATAGAAGGTG | 180 |
| CAGCCGAAAT | AGCGGACAAA | TTGAAGTGGA | TACCTGAAGT | ATCAGTGTCT | TCAAGTCATT | 240 |
| CTTCAGTGTC | ATCTT | | | | | 255 |

( 2 ) INFORMATION FOR SEQ ID NO:8:

( i ) SEQUENCE CHARACTERISTICS:
        ( A ) LENGTH: 245 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

| GAATTCAACT | GTAGCTTGGT | TTTCCAAAGT | ATCTGGATCT | AGTATTTCAG | TCTTTTTGTC | 60 |
| TTCTTCAGCA | CAACATTTTA | CACAGACATA | TTCTTTGTCT | TCCTCGCCCA | TCTGCTGTGC | 120 |
| TTGAGAAAGA | CTTAACCCAA | CACAATCACC | ATGAAACCAG | TCATCACATC | TCCACAGCCA | 180 |
| ACCATAACTG | TTGCATGTGT | TTTTGCAAAC | CACACTGTTG | CTGGAGTCAC | ATATATTCGT | 240 |
| TCAAT | | | | | | 245 |

( 2 ) INFORMATION FOR SEQ ID NO:9:

( i ) SEQUENCE CHARACTERISTICS:
        ( A ) LENGTH: 688 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| GAATTCAGTG | GAGCACCAGT | AGAAGGTGCA | GGAGAAGAGG | CATTGACTCC | ATCAGTTCCT | 60 |
| ATAAATAAAG | GTCCCAAACC | TAAGAGGGAG | AAGAAGGAGC | CTGGTACCAG | AGTGAGAAAA | 120 |
| ACACCTACAT | CATCTGGTAA | ACCTAGTGCA | AAGAAAGTGA | AGAAACGGAA | TCCTTGGTCA | 180 |
| GATGATGAAT | CCAAGTCAGA | AAGTGATTTG | GAAGAAACAG | AACCTGTGGT | TATTCCAAGA | 240 |
| GATTCTTTGC | TTAGGAGAGC | AGCAGCCGAA | AGACCTAAAT | ACACATTTAA | TTTCTCAGAA | 300 |

| | | | | | | |
|---|---|---|---|---|---|---|
| GAAGAGGATG | ATGATGCTGA | TGATGATGAT | GATGACAATA | ATGATTTAGA | GGAATTGAAA | 360 |
| GTTAAAGCAT | CTCCCATAAC | AAATGATGGG | GAAGATGAAT | TTGTTCCTTC | AGATGGGTTA | 420 |
| GATAAAGATG | AATATACATT | TTCACCAGGC | AAATCAAAAG | CCTCACCAGA | AAAATCTTTG | 480 |
| CATGACAAAA | AAAGTCAGGA | TTTTGGAAAT | CTCTTCTCAT | TTCCTTCATA | TTCTCAGAAG | 540 |
| TCAGAAGATG | ATTCAGCTAA | ATTTGACAGT | AATGAAGAAG | ATTCTGCTTC | TGTTTTTTCA | 600 |
| CCATCATTTG | GTCTGAAACA | GACAGATAAA | GTTCCAAGTA | AACGGTAGC | TGCTAAAAAG | 660 |
| GGAAAACCGT | CTTCAGATAC | AGTCCCTA | | | | 688 |

( 2 ) INFORMATION FOR SEQ ID NO:10:

( i ) SEQUENCE CHARACTERISTICS:
        ( A ) LENGTH: 348 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | | |
|---|---|---|---|---|---|---|
| GCAATGTTTA | ATTAAGTGGG | GAAAGAGCAC | AAACATTTTT | CAACAAATAC | TTGTGTTGTC | 60 |
| CTTTTGTCTT | CTCTGTCTCA | GACCTTTGT | ACATCTGGCT | TATTTTAATG | TGATGATGTA | 120 |
| ATTGACCGTT | TTTTATTATT | GTGGTAGGCC | TTTTAACATT | TTGTTCTTAC | ACATACAGTT | 180 |
| TTATGCTCTT | TTTTACTCAT | TGAAATGTCA | CGTACTGTCT | GATTGGCTTG | TAGAATTGGT | 240 |
| TATAGACTGC | CGTGCATTAG | CACAGATTTT | AATTGTCATG | GTTACAAACT | ACAGACCTGC | 300 |
| TTTTTGAAAT | GAAATTTAAA | CATTAAAAAT | GGAACTGTGA | AAAAAAA | | 348 |

( 2 ) INFORMATION FOR SEQ ID NO:11:

( i ) SEQUENCE CHARACTERISTICS:
        ( A ) LENGTH: 1800 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

| | | | | | | |
|---|---|---|---|---|---|---|
| GAATTCCGGG | CCAAGAAGCC | TAATGAGAAA | AACAAACCAC | TTGATAATAA | GGGAGAAAAA | 60 |
| AGAAAAAGAA | AAACTGAAGA | AAAAGGCGTA | GATAAAGATT | TTGAGTCTTC | TTCAATGAAA | 120 |
| ATCTCGAAAC | TAGAAGTGAC | TGAAATAGTG | AAACCATCAC | CAAAGCGCAA | AATGGAACCT | 180 |
| GATACTGAAA | AAATGGATAG | GACCCCTGAA | AAGGACAAAA | TTTCTTTAAG | TGCGCCAGCC | 240 |
| AAAAAAATCA | AACTCAACAG | AGAAACTGGG | AAGAAAATTG | GAAGTACAGA | AAATATATCA | 300 |
| AACACAAAAG | AACCCTCTGA | AAAATTGGAG | TCAACATCTA | GCAAAGTTAA | ACAAGAAAAA | 360 |
| GTCAAAGGAA | AGGTCAGACG | AAAAGTGACT | GGAACTGAAG | GATCCAGCTC | AACTCTGGTG | 420 |
| GATTACACCA | GTACGAGCTC | AACTGGAGGC | AGTCCTGTGC | GGAAATCTGA | AGAAAAAACA | 480 |
| GATACAAAGC | GAACTGTGAT | TAAAAGCATG | GAAGAATATA | ATAATGACAA | TACCGCGCCA | 540 |
| CGTGAAGATG | TTATCATTAT | GATTCAGGTT | CCTCAATCCA | AATGGGATAA | AGATGACTTT | 600 |
| GAATCTGAAG | AAGAAGATGT | TAAATCCACA | CAGCCTATAT | CAAGTGTAGG | AAAACCTGCT | 660 |
| AGTGTTATAA | AAAATGTTAG | TACAAAGCCA | TCAAATATAG | TCAAGTATCC | TGAGAAAGAA | 720 |
| AGTGAGCCAT | CCGAGAAAAT | TCAGAAATTC | ACCAAGGACG | TGAGCCATGA | AATCATACAA | 780 |
| CATGAGGTTA | AAAGTTCAAA | AAACTCTGCA | TCTAGTGAAA | AAGGGAAAAC | CAAAGATCGA | 840 |

| | | | | | | |
|---|---|---|---|---|---|---|
| GATTATTCAG | TGTTGGAAAA | GGAGAACCCT | GAAAGAGGA | AGAACAGCAC | TCAGCCAGAG | 900 |
| AAAGAGAGTA | ATTTGGACCG | TCTGAATGAA | CAAGGAAATT | TTAAAAGTCT | GTCTCAATCT | 960 |
| TCCAAAGAGG | CTAGAACGTC | AGATAAACAT | GATTCCACTC | GTGCTTCCTC | AAATAAAGAC | 1020 |
| TTCACTCCCA | ATAGAGACAA | AAAAACTGAC | TATGACACCA | GAGAGTATTC | AAGTTCCAAA | 1080 |
| CGTAGAGATG | AAAAGAATGA | ATTAACAAGA | CGAAAGACT | CTCCTTCTCG | GAATAAAGAT | 1140 |
| TCTGCATCTG | GACAGAAAAA | TAAACCAAGG | GAAGAGAGAG | ATTTGCCTAA | AAAAGGAACA | 1200 |
| GGAGATTCCA | AAAAAAGTAA | TTCTAGTCCC | TCAAGAGACA | GAAAACCTCA | TGATCACAAA | 1260 |
| GCCACTTATG | ATACTAAACG | GCCAAATGAA | GAGACAAAAT | CTGTAGATAA | AAATCCTTGT | 1320 |
| AAGGATCGTG | AGAAGCATGT | ATTAGAAGCA | AGGAACAATA | AGAGTCAAG | TGGCAATAAA | 1380 |
| CTACTTTATA | TACTTAACCC | ACCAGAGACA | CAGGTTGAAA | AAGAGCAAAT | TACTGGGCAA | 1440 |
| ATTGACAAGA | GTACTGTCAA | GCCTAAACCC | CAGTTAAGTC | ATTCCTCTAG | ACTTTCCTCT | 1500 |
| GACTTAACTA | GAGAAACTCA | TGAAGCTGCT | TTTGAACCAG | ACTATAATGA | AAGTGACAGT | 1560 |
| GAAAGTAATG | TTTCTGTAAA | AGAAGAGGAA | TCTTCAGGAA | ACATTTCTAA | GGACCTGAAA | 1620 |
| GATAAAATAG | TGGAGAAAGC | AAAAGAGAGC | CTGGACACAG | CAGCAGTTGT | CCAGGTGGGC | 1680 |
| ATAAGCAGGA | ATCAGAGCCA | CAGCAGCCCC | AGCGTCAGCC | CCAGCAGAAG | CCACAGTCCT | 1740 |
| TCTGGAAGCC | AGACCCGAAG | CCACAGTAGC | AGTGCCAGCT | CAGCAGAAAG | TCAGGACAGC | 1800 |

( 2 ) INFORMATION FOR SEQ ID NO:12:

( i ) SEQUENCE CHARACTERISTICS:
        ( A ) LENGTH: 4868 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| GAATTCCGGC | CGGAATTAAT | TCCGGGGATT | TCCTGGGGAA | TCAGGAAGAT | ATCCATAATC | 60 |
| TTCAACTGCG | GGTAAAAGAG | ACATCAAATG | AGAATTTGAG | ATTACTTCAT | GTGATAGAGG | 120 |
| ACCGTGACAG | AAAAGTTGAA | AGTTTGCTAA | ATGAAATGAA | AGAATTAGAC | TCAAAACTCC | 180 |
| ATTTACAGGA | GGTACAACTA | ATGACCAAAA | TTGAAGCATG | CATAGAATTG | GAAAAAATAG | 240 |
| TTGGGGAACT | TAAGAAAGAA | AACTCAGATT | TAAGTGAAAA | ATTGGAATAT | TTTTCTTGTG | 300 |
| ATCACCAGGA | GTTACTCCAG | AGAGTAGAAA | CTTCTGAAGG | CCTCAATTCT | GATTTAGAAA | 360 |
| TGCATGCAGA | TAAATCATCA | CGTGAAGATA | TTGGAGATAA | TGTGGCCAAG | GTGAATGACA | 420 |
| GCTGGAAGGA | GAGATTTCTT | GATGTGGAAA | ATGAGCTGAG | TAGGATCAGA | TCGGAGAAAG | 480 |
| CTAGCATTGA | GCATGAAGCC | CTCTACCTGG | AGGCTGACTT | AGAGGTAGTT | CAAACAGAGA | 540 |
| AGCTATGTTT | AGAAAAAGAC | AATGAAAATA | AGCAGAAGGT | TATTGTCTGC | CTTGAAGAAG | 600 |
| AACTCTCAGT | GGTCACAAGT | GAGAGAAACC | AGCTTCGTGG | AGAATTAGAT | ACTATGTCAA | 660 |
| AAAAAACCAC | GGCACTGGAT | CAGTTGTCTG | AAAAAATGAA | GGAGAAAACA | CAAGAGCTTG | 720 |
| AGTCTCATCA | AAGTGAGTGT | CTCCATTGCA | TTCAGGTGGC | AGAGGCAGAG | GTGAAGGAAA | 780 |
| AGACGGAACT | CCTTCAGACT | TTGTCCTCTG | ATGTGAGTGA | GCTGTTAAAA | GACAAAACTC | 840 |
| ATCTCCAGGA | AAAGCTGCAG | AGTTTGGAAA | AGGACTCACA | GGCACTGTCT | TTGACAAAAT | 900 |
| GTGAGCTGGA | AAACCAAATT | GCACAACTGA | ATAAAGAGAA | AGAATTGCTT | GTCAAGGAAT | 960 |
| CTGAAAGCCT | GCAGGCCAGA | CTGAGTGAAT | CAGATTATGA | AAAGCTGAAT | GTCTCCAAGG | 1020 |
| CCTTGGAGGC | CGCACTGGTG | GAGAAAGGTG | AGTTCGCATT | GAGGCTGAGC | TCAACACAGG | 1080 |

| | | | | | | |
|---|---|---|---|---|---|---|
| AGGAAGTGCA | TCAGCTGAGA | AGAGGCATCG | AGAAACTGAG | AGTTCGCATT | GAGGCCGATG | 1140 |
| AAAAGAAGCA | GCTGCACATC | GCAGAGAAAC | TGAAAGAACG | CGAGCGGGAG | AATGATTCAC | 1200 |
| TTAAGGTAAA | AGTTGAGAAC | CTTGAAAGGG | AATTGCAGAT | GTCAGAAGAA | AACCAGGAGC | 1260 |
| TAGTGATTCT | TGATGCCGAG | AATTCCAAAG | CAGAAGTAGA | GACTCTAAAA | ACACAAATAG | 1320 |
| AAGAGATGGC | CAGAAGCCTG | AAAGTTTTTG | AATTAGACCT | TGTCACGTTA | AGGTCTGAAA | 1380 |
| AAGAAAATCT | GACAAAACAA | ATACAAGAAA | AACAAGGTCA | GTTGTCAGAA | CTAGACAAGT | 1440 |
| TACTCTCTTC | ATTTAAAAGT | CTGTTAGAAG | AAAAGGAGCA | AGCAGAGATA | CAGATCAAAG | 1500 |
| AAGAATCTAA | AACTGCAGTG | GAGATGCTTC | AGAATCAGTT | AAAGGAGCTA | AATGAGGCAG | 1560 |
| TAGCAGCCTT | GTGTGGTGAC | CAAGAAATTA | TGAAGGCCAC | AGAACAGAGT | CTAGACCCAC | 1620 |
| CAATAGAGGA | AGAGCATCAG | CTGAGAAATA | GCATTGAAAA | GCTGAGAGCC | CGCCTAGAAG | 1680 |
| CTGATGAAAA | GAAGCAGCTC | TGTGTCTTAC | AACAACTGAA | GGAAAGTGAG | CATCATGCAG | 1740 |
| ATTTACTTAA | GGGTAGAGTG | GAGAACCTTG | AAAGAGAGCT | AGAGATAGCC | AGGACAAACC | 1800 |
| AAGAGCATGC | AGCTCTTGAG | GCAGAGAATT | CCAAAGGAGA | GGTAGAGACC | CTAAAAGCAA | 1860 |
| AAATAGAAGG | GATGACCCAA | AGTCTGAGAG | GTCTGGAATT | AGATGTTGTT | ACTATAAGGT | 1920 |
| CAGAAAAAGA | AAATCTGACA | AATGAATTAC | AAAAAGAGCA | AGAGCGAATA | TCTGAATTAG | 1980 |
| AAATAATAAA | TTCATCATTT | GAAAATATTT | TGCAAGAAAA | AGAGCAAGAG | AAAGTACAGA | 2040 |
| TGAAAGAAAA | ATCAAGCACT | GCCATGGAGA | TGCTTCAAAC | ACAATTAAAA | GAGCTCAATG | 2100 |
| AGAGAGTGGC | AGCCCTGCAT | AATGACCAAG | AAGCCTGTAA | GGCCAAAGAG | CAGAATCTTA | 2160 |
| GTAGTCAAGT | AGAGTGTCTT | GAACTTGAGA | AGGCTCAGTT | GCTACAAGGC | CTTGATGAGG | 2220 |
| CCAAAAATAA | TTATATTGTT | TTGCAATCTT | CAGTGAATGG | CCTCATTCAA | GAAGTAGAAG | 2280 |
| ATGGCAAGCA | GAAACTGGAG | AAGAAGGATG | AAGAAATCAG | TAGACTGAAA | AATCAAATTC | 2340 |
| AAGACCAAGA | GCAGCTTGTC | TCTAAACTGT | CCCAGGTGGA | AGGAGAGCAC | CAACTTTGGA | 2400 |
| AGGAGCAAAA | CTTAGAACTG | AGAAATCTGA | CAGTGGAATT | GGAGCAGAAG | ATCCAAGTGC | 2460 |
| TACAATCCAA | AAATGCCTCT | TTGCAGGACA | CATTAGAAGT | GCTGCAGAGT | TCTTACAAGA | 2520 |
| ATCTAGAGAA | TGAGCTTGAA | TTGACAAAAA | TGGACAAAAT | GTCCTTTGTT | GAAAAAGTAA | 2580 |
| ACAAAATGAC | TGCAAAGGAA | ACTGAGCTGC | AGAGGGAAAT | GCATGAGATG | GCACAGAAAA | 2640 |
| CAGCAGAGCT | GCAAGAAGAA | CTCAGTGGAG | AGAAAAATAG | GCTAGCTGGA | GAGTTGCAGT | 2700 |
| TACTGTTGGA | AGAAATAAAG | AGCAGCAAAG | ATCAATTGAA | GGAGCTCACA | CTAGAAAATA | 2760 |
| GTGAATTGAA | GAAGAGCCTA | GATTGCATGC | ACAAAGACCA | GGTGGAAAAG | GAAGGGAAAG | 2820 |
| TGAGAGAGGA | AATAGCTGAA | TATCAGCTAC | GGCTTCATGA | AGCTGAAAAG | AAACACCAGG | 2880 |
| CTTTGCTTTT | GGACACAAAC | AAACAGTATG | AAGTAGAAAT | CCAGACATAC | CGAGAGAAAT | 2940 |
| TGACTTCTAA | AGAAGAATGT | CTCAGTTCAC | AGAAGCTGGA | GATAGACCTT | TTAAAGTCTA | 3000 |
| GTAAAGAAGA | GCTCAATAAT | TCATTGAAAG | CTACTACTCA | GATTTTGGAA | GAATTGAAGA | 3060 |
| AAACCAAGAT | GGACAATCTA | AAATATGTAA | ATCAGTTGAA | GAAGGAAAAT | GAACGTGCCC | 3120 |
| AGGGGAAAAT | GAAGTTGTTG | ATCAAATCCT | GTAAACAGCT | GGAAGAGGAA | AAGGAGATAC | 3180 |
| TGCAGAAAGA | ACTCTCTCAA | CTTCAAGCTG | CACAGGAGAA | GCAGAAAACA | GGTACTGTTA | 3240 |
| TGGATACCAA | GGTCGATGAA | TTAACAACTG | AGATCAAAGA | ACTGAAAGAA | ACTCTTGAAG | 3300 |
| AAAAAACCAA | GGAGGCAGAT | GAATACTTGG | ATAAGTACTG | TTCCTTGCTT | ATAAGCCATG | 3360 |
| AAAAGTTAGA | GAAAGCTAAA | GAGATGTTAG | AGACACAAGT | GGCCCATCTG | TGTTCACAGC | 3420 |
| AATCTAAACA | AGATTCCCGA | GGGTCTCCTT | TGCTAGGTCC | AGTTGTTCCA | GGACCATCTC | 3480 |

-continued

| | | | | | |
|---|---|---|---|---|---|
| CAATCCCTTC | TGTTACTGAA | AAGAGGTTAT | CATCTGGCCA | AAATAAAGCT | TCAGGCAAGA | 3540
| GGCAAAGATC | CAGTGGAATA | TGGGAGAATG | GTGGAGGACC | AACACCTGCT | ACCCCAGAGA | 3600
| CCTTTTCTAA | AAAAAGCAAG | AAAGCAGTCA | TGAGTGGTAT | TCACCCTGCA | GAAGACACGG | 3660
| AAGGTACTGA | GTTTGAGCCA | GAGGGACTTC | AGAAGTTGT | AAAGAAAGGG | TTTGCTGACA | 3720
| TCCCGACAGG | AAAGACTAGC | CCATATATCC | TGCGAAGAAC | AACCATGGCA | ACTGGGAGCA | 3780
| GGCCCGGCCT | GGCTGCACAC | AAGTTACCCC | TATCCCACT | GACTGTCCCC | AAACAAATC | 3840
| TTGCAGAGTC | CTCCAAACCA | ACAGCTGGTG | GCAGCAGATC | ACAAAAGGTG | AAAGTTGCTC | 3900
| AGCGGAGCCC | AGTAGATTCA | GGCACCATCC | TCCGAGAACC | CACCACGAAA | TCCGTCCCAG | 3960
| TCAATAATCT | TCCTGAGAGA | AGTCCGACTG | ACAGCCCAG | AGAGGGCCTG | AGGGTCAAGC | 4020
| GCCGGCGACT | TGTCCCCAGC | CCCAAAGCTG | GACTGGAGTC | CAAGGGCAGT | GAGAACTGTA | 4080
| AGGTCCAGTG | AAGGCACTTT | GTGTGTCAGT | ACCCCTGGGA | GGTGCCAGTC | ATTGAATAGA | 4140
| TAAGGCTGTG | CCTACAGGAC | TTCTCTTTAG | TCAGGGCATG | CTTTATTAGT | GAGGAGAAAA | 4200
| CAATTCCTTA | GAAGTCTTAA | ATATATTGTA | CTCTTTAGAT | CTCCATGTG | TAGGTATTGA | 4260
| AAAAGTTTGG | AAGCACTGAT | CACCTGTTAG | CATTGCAATT | CCTCTACTGC | AATGTAAATA | 4320
| GTATAAAGCT | ATGTATATAA | AGCTTTTGG | TAATATGTTA | CAATTAAAAT | GACAAGCACT | 4380
| ATATCACAAT | CTCTGTTTGT | ATGTGGGTTT | TACACTAAAA | AAATGCAAAA | CACATTTTAT | 4440
| TCTTCTAATT | AACAGCTCCT | AGGAAAATGT | AGACTTTGC | TTTATGATAT | TCTATCTGTA | 4500
| GTATGAGGCA | TGGAATAGTT | TTGTATCGGG | AATTTCTCAG | AGCTGAGTAA | AATGAAGGAA | 4560
| AAGCATGTTA | TGTGTTTTA | AGGAAAATGT | GCACACATAT | ACATGTAGGA | GTGTTTATCT | 4620
| TTCTCTTACA | ATCTGTTTTA | GACATCTTTG | CTTATGAAAC | CTGTACATAT | GTGTGTGTGG | 4680
| GTATGTGTTT | ATTTCCAGTG | AGGGCTGCAG | GCTTCCTAGA | GGTGTGCTAT | ACCATGCGTC | 4740
| TGTCGTTGTG | CTTTTTTCTG | TTTTTAGACC | AATTTTTTAC | AGTTCTTTGG | TAAGCATTGT | 4800
| CGTATCTGGT | GATGGATTAA | CATATAGCCT | TTGTTTTCTA | ATAAAATAGT | CGCCTTCGTA | 4860
| AAAAAAA | | | | | | 4868

( 2 ) INFORMATION FOR SEQ ID NO:13:

( i ) SEQUENCE CHARACTERISTICS:
        ( A ) LENGTH: 2492 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1428

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| CTT | TGC | AGG | CAG | CGG | CGG | CCG | GGG | GCG | GAG | CGG | GAT | CGA | GCC | CTC | GCC | 48
| Leu | Cys | Arg | Gln | Arg | Arg | Pro | Gly | Ala | Glu | Arg | Asp | Arg | Ala | Leu | Ala |
| 1 | | | | 5 | | | | | 10 | | | | | 15 | | |
| GAG | GCC | TGC | CGC | CAT | GGG | CCC | GCG | CCG | CCG | CCG | CCT | GTC | ACC | CGG | | 96
| Glu | Ala | Cys | Arg | His | Gly | Pro | Ala | Pro | Pro | Pro | Pro | Val | Thr | Arg | |
| | | | 20 | | | | 25 | | | | | 30 | | | | |
| GCC | GCG | CGG | GCC | GTG | AGC | GTC | ATG | GCC | TTG | GCC | GGG | GCC | CCT | GCG | GGC | 144
| Ala | Ala | Arg | Ala | Val | Ser | Val | Met | Ala | Leu | Ala | Gly | Ala | Pro | Ala | Gly |
| | | | | 35 | | | | 40 | | | | | 45 | | | |
| GGC | CCA | TGC | GCG | CCG | GCG | CTG | GAG | GCC | CTG | CTC | GGG | GCC | GGC | GCG | CTG | 192
| Gly | Pro | Cys | Ala | Pro | Ala | Leu | Glu | Ala | Leu | Leu | Gly | Ala | Gly | Ala | Leu |

-continued

|  | 50 |  |  |  | 55 |  |  |  | 60 |  |  |  |  |  |  |  |
|---|---|---|---|---|---|---|---|---|---|---|---|---|---|---|---|---|
| CGG | CTG | CTC | GAC | TCC | TCG | CAG | ATC | GTC | ATC | ATC | TCC | GCC | GCG | CAG | GAC | 240 |
| Arg | Leu | Leu | Asp | Ser | Ser | Gln | Ile | Val | Ile | Ile | Ser | Ala | Ala | Gln | Asp |  |
| 65 |  |  |  | 70 |  |  |  |  | 75 |  |  |  |  |  | 80 |  |
| GCC | AGC | GCC | CCG | CCG | GCT | CCC | ACC | GGC | CCG | GCG | CCC | GCC | GCC | GGC |  | 288 |
| Ala | Ser | Ala | Pro | Pro | Ala | Pro | Thr | Gly | Pro | Ala | Ala | Pro | Ala | Gly |  |  |
|  |  |  | 85 |  |  |  |  | 90 |  |  |  |  |  | 95 |  |  |
| CCC | TGC | GAC | CCT | GAC | CTG | CTG | CTC | TTC | GCC | ACA | CCG | CAG | GCG | CCC | CGG | 336 |
| Pro | Cys | Asp | Pro | Asp | Leu | Leu | Leu | Phe | Ala | Thr | Pro | Gln | Ala | Pro | Arg |  |
|  |  |  | 100 |  |  |  |  | 105 |  |  |  |  | 110 |  |  |  |
| CCC | ACA | CCC | AGT | GCG | CCG | CGG | CCC | GCG | CTC | GGC | CGC | CCG | CCG | GTG | AAG | 384 |
| Pro | Thr | Pro | Ser | Ala | Pro | Arg | Pro | Ala | Leu | Gly | Arg | Pro | Pro | Val | Lys |  |
|  |  |  | 115 |  |  |  |  | 120 |  |  |  |  | 125 |  |  |  |
| CGG | AGG | CTG | GAC | CTG | GAA | ACT | GAC | CAT | CAG | TAC | CTG | GCC | GAG | AGC | AGT | 432 |
| Arg | Arg | Leu | Asp | Leu | Glu | Thr | Asp | His | Gln | Tyr | Leu | Ala | Glu | Ser | Ser |  |
|  | 130 |  |  |  |  | 135 |  |  |  |  | 140 |  |  |  |  |  |
| GGG | CCA | GCT | CGG | GGC | AGA | GGC | CGC | CAT | CCA | GGA | AAA | GGT | GTG | AAA | TCC | 480 |
| Gly | Pro | Ala | Arg | Gly | Arg | Gly | Arg | His | Pro | Gly | Lys | Gly | Val | Lys | Ser |  |
| 145 |  |  |  |  | 150 |  |  |  |  | 155 |  |  |  |  | 160 |  |
| CCG | GGG | GAG | AAG | TCA | CGC | TAT | GAG | ACC | TCA | CTG | AAT | CTG | ACC | ACC | AAG | 528 |
| Pro | Gly | Glu | Lys | Ser | Arg | Tyr | Glu | Thr | Ser | Leu | Asn | Leu | Thr | Thr | Lys |  |
|  |  |  |  | 165 |  |  |  |  | 170 |  |  |  |  | 175 |  |  |
| CGC | TTC | CTG | GAG | CTG | CTG | AGC | CAC | TCG | GCT | GAC | GGT | GTC | GTC | GAC | CTG | 576 |
| Arg | Phe | Leu | Glu | Leu | Leu | Ser | His | Ser | Ala | Asp | Gly | Val | Val | Asp | Leu |  |
|  |  |  | 180 |  |  |  |  | 185 |  |  |  |  | 190 |  |  |  |
| AAC | TGG | GCT | GCC | GAG | GTG | CTG | AAG | GTG | CAG | AAG | CGG | CGC | ATC | TAT | GAC | 624 |
| Asn | Trp | Ala | Ala | Glu | Val | Leu | Lys | Val | Gln | Lys | Arg | Arg | Ile | Tyr | Asp |  |
|  |  |  | 195 |  |  |  |  | 200 |  |  |  |  | 205 |  |  |  |
| ATC | ACC | AAC | GTC | CTT | GAG | GGC | ATC | CAG | CTC | ATT | GCC | AAG | AAG | TCC | AAG | 672 |
| Ile | Thr | Asn | Val | Leu | Glu | Gly | Ile | Gln | Leu | Ile | Ala | Lys | Lys | Ser | Lys |  |
| 210 |  |  |  |  |  | 215 |  |  |  |  | 220 |  |  |  |  |  |
| AAC | CAC | ATC | CAG | TGG | CTG | GGC | AGC | CAC | ACC | ACA | GTG | GGC | GTC | GGC | GGA | 720 |
| Asn | His | Ile | Gln | Trp | Leu | Gly | Ser | His | Thr | Thr | Val | Gly | Val | Gly | Gly |  |
| 225 |  |  |  |  | 230 |  |  |  |  | 235 |  |  |  |  | 240 |  |
| CGG | CTT | GAG | GGG | TTG | ACC | CAG | GAC | CTC | CGA | CAG | CTG | CAG | GAG | AGC | GAG | 768 |
| Arg | Leu | Glu | Gly | Leu | Thr | Gln | Asp | Leu | Arg | Gln | Leu | Gln | Glu | Ser | Glu |  |
|  |  |  |  | 245 |  |  |  |  | 250 |  |  |  |  | 255 |  |  |
| CAG | CAG | CTG | GAC | CAC | CTG | ATG | AAT | ATC | TGT | ACT | ACG | CAG | CTG | CGC | CTG | 816 |
| Gln | Gln | Leu | Asp | His | Leu | Met | Asn | Ile | Cys | Thr | Thr | Gln | Leu | Arg | Leu |  |
|  |  |  | 260 |  |  |  |  | 265 |  |  |  |  | 270 |  |  |  |
| CTC | TCC | GAG | GAC | ACT | GAC | AGC | CAG | CGC | CTG | GCC | TAC | GTG | ACG | TGT | CAG | 864 |
| Leu | Ser | Glu | Asp | Thr | Asp | Ser | Gln | Arg | Leu | Ala | Tyr | Val | Thr | Cys | Gln |  |
|  |  |  | 275 |  |  |  |  | 280 |  |  |  |  | 285 |  |  |  |
| GAC | CTT | CGT | AGC | ATT | GCA | GAC | CCT | GCA | GAG | CAG | ATG | GTT | ATG | GTG | ATC | 912 |
| Asp | Leu | Arg | Ser | Ile | Ala | Asp | Pro | Ala | Glu | Gln | Met | Val | Met | Val | Ile |  |
|  | 290 |  |  |  |  | 295 |  |  |  |  | 300 |  |  |  |  |  |
| AAA | GCC | CCT | CCT | GAG | ACC | CAG | CTC | CAA | GCC | GTG | GAC | TCT | TCG | GAG | AAC | 960 |
| Lys | Ala | Pro | Pro | Glu | Thr | Gln | Leu | Gln | Ala | Val | Asp | Ser | Ser | Glu | Asn |  |
| 305 |  |  |  |  | 310 |  |  |  |  | 315 |  |  |  |  | 320 |  |
| TTT | CAG | ATC | TCC | CTT | AAG | AGC | AAA | CAA | GGC | CCG | ATC | GAT | GTT | TTC | CTG | 1008 |
| Phe | Gln | Ile | Ser | Leu | Lys | Ser | Lys | Gln | Gly | Pro | Ile | Asp | Val | Phe | Leu |  |
|  |  |  |  | 325 |  |  |  |  | 330 |  |  |  |  | 335 |  |  |
| TGC | CCT | GAG | GAG | ACC | GTA | GGT | GGG | ATC | AGC | CCT | GGG | AAG | ACC | CCA | TCC | 1056 |
| Cys | Pro | Glu | Glu | Thr | Val | Gly | Gly | Ile | Ser | Pro | Gly | Lys | Thr | Pro | Ser |  |
|  |  |  |  | 340 |  |  |  |  | 345 |  |  |  |  | 350 |  |  |
| CAG | GAG | GTC | ACT | TCT | GAG | GAG | GAG | AAC | AGG | GCC | ACT | GAC | TCT | GCC | ACC | 1104 |
| Gln | Glu | Val | Thr | Ser | Glu | Glu | Glu | Asn | Arg | Ala | Thr | Asp | Ser | Ala | Thr |  |
|  |  |  | 355 |  |  |  |  | 360 |  |  |  |  | 365 |  |  |  |
| ATA | GTG | TCA | CCA | CCA | CCA | TCA | TCT | CCC | CCC | TCA | TCC | CTC | ACC | ACA | GAT | 1152 |
| Ile | Val | Ser | Pro | Pro | Pro | Ser | Ser | Pro | Pro | Ser | Ser | Leu | Thr | Thr | Asp |  |

```
                     370                          375                          380
CCC  AGC  CAG  TCT  CTA  CTC  AGC  CTG  GAG  CAA  GAA  CCG  CTG  TTG  TCC  CGG         1200
Pro  Ser  Gln  Ser  Leu  Leu  Ser  Leu  Glu  Gln  Glu  Pro  Leu  Leu  Ser  Arg
385                      390                          395                      400

ATG  GGC  AGC  CTG  CGG  GCT  CCC  GTG  GAC  GAG  GAC  CGC  CTG  TCC  CCG  CTG         1248
Met  Gly  Ser  Leu  Arg  Ala  Pro  Val  Asp  Glu  Asp  Arg  Leu  Ser  Pro  Leu
                    405                      410                          415

GTG  GCG  GCC  GAC  TCG  CTC  CTG  GAG  CAT  GTG  CGG  GAG  GAC  TTC  TCC  GGC         1296
Val  Ala  Ala  Asp  Ser  Leu  Leu  Glu  His  Val  Arg  Glu  Asp  Phe  Ser  Gly
               420                           425                     430

CTC  CTC  CCT  GAG  GAG  TTC  ATC  AGC  CTT  TCC  CCA  CCC  CAC  GAG  GCC  CTC         1344
Leu  Leu  Pro  Glu  Glu  Phe  Ile  Ser  Leu  Ser  Pro  Pro  His  Glu  Ala  Leu
          435                         440                      445

GAC  TAC  CAC  TTC  GGC  CTC  GAG  GAG  GGC  GAG  GGC  ATC  AGA  GAC  CTC  TTC         1392
Asp  Tyr  His  Phe  Gly  Leu  Glu  Glu  Gly  Glu  Gly  Ile  Arg  Asp  Leu  Phe
     450                          455                     460

GAC  TGT  GAC  TTT  GGG  GAC  CTC  ACC  CCC  CTG  GAT  TTC  TGACAGGGCT                  1438
Asp  Cys  Asp  Phe  Gly  Asp  Leu  Thr  Pro  Leu  Asp  Phe
465                      470                      475

TGGAGGGACC  AGGGTTTCCA  GAGATGCTCA  CCTTGTCTCT  GCAGCCCTGG  AGCCCCTGT                  1498
CCCTGGCCGT  CCTCCCAGCC  TGTTTGGAAA  CATTTAATTT  ATACCCCTCT  CCTCTGTCTC                  1558
CAGAAGCTTC  TAGCTCTGGG  GTCTGGCTAC  CGCTAGGAGG  CTGAGCAAGC  CAGGAAGGGA                  1618
AGGAGTCTGT  GTGGTGTGTA  TGTGCATGCA  GCCTACACCC  ACACGTGTGT  ACCGGGGGTG                  1678
AATGTGTGTG  AGCATGTGTG  TGTGCATGTA  CCGGGGAATG  AAGGTGAACA  TACACCTCTG                  1738
TGTGTGCACT  GCAGACACGC  CCCAGTGTGT  CCACATGTGT  GTGCATGAGT  CCATGTGTGC                  1798
GCGTGGGGGG  GCTCTAACTG  CACTTTCGGC  CCTTTTGCTC  TGGGGGTCCC  ACAAGGCCCA                  1858
GGGCAGTGCC  TGCTCCCAGA  ATCTGGTGCT  CTGACCAGGC  CAGGTGGGGA  GGCTTTGGCT                  1918
GGCTGGGCGT  GTAGGACGGT  GAGAGCACTT  CTGTCTTAAA  GGTTTTTTCT  GATTGAAGCT                  1978
TTAATGGAGC  GTTATTTATT  TATCGAGGCC  TCTTTGGTGA  GCCTGGGGAA  TCAGCAAAGG                  2038
GGAGGAGGGG  TGTGGGGTTG  ATACCCCAAC  TCCCTCTACC  CTTGAGCAAG  GGCAGGGGTC                  2098
CCTGAGCTGT  TCTTCTGCCC  CATACTGAAG  GAACTGAGGC  CTGGGTGATT  TATTTATTGG                  2158
GAAAGTGAGG  GAGGGAGACA  GACTGACTGA  CAGCCATGGG  TGGTCAGATG  GTGGGGTGGG                  2218
CCCTCTCCAG  GGGGCCAGTT  CAGGGCCCCA  GCTGCCCCCC  AGGATGGATA  TGAGATGGGA                  2278
GAGGTGAGTG  GGGGACCTTC  ACTGATGTGG  GCAGGAGGGG  TGGTGAAGGC  CTCCCCCAGC                  2338
CCAGACCCTG  TGGTCCCTCC  TGCAGTGTCT  GAAGCGCCTG  CCTCCCACT  GCTCTGCCCC                   2398
ACCCTCCAAT  CTGCACTTTG  ATTTGCTTCC  TAACAGCTCT  GTTCCCTCCT  GCTTTGGTTT                  2458
TAATAAATAT  TTTGATGACG  TTAAAAAAAA  AAAA                                                2492
```

( 2 ) INFORMATION FOR SEQ ID NO:14:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Leu  Cys  Arg  Gln  Arg  Arg  Pro  Gly  Ala  Glu  Arg  Asp  Arg  Ala  Leu  Ala
  1                 5                          10                          15

Glu  Ala  Cys  Arg  His  Gly  Pro  Ala  Pro  Pro  Pro  Pro  Val  Thr  Arg
               20                           25                     30
```

```
Ala Ala Arg Ala Val Ser Val Met Ala Leu Ala Gly Ala Pro Ala Gly
         35                  40                  45
Gly Pro Cys Ala Pro Ala Leu Glu Ala Leu Leu Gly Ala Gly Ala Leu
     50                  55                  60
Arg Leu Leu Asp Ser Ser Gln Ile Val Ile Ile Ser Ala Ala Gln Asp
 65                  70                  75                  80
Ala Ser Ala Pro Pro Ala Pro Thr Gly Pro Ala Ala Pro Ala Ala Gly
             85                  90                  95
Pro Cys Asp Pro Asp Leu Leu Leu Phe Ala Thr Pro Gln Ala Pro Arg
            100                 105                 110
Pro Thr Pro Ser Ala Pro Arg Pro Ala Leu Gly Arg Pro Pro Val Lys
            115                 120                 125
Arg Arg Leu Asp Leu Glu Thr Asp His Gln Tyr Leu Ala Glu Ser Ser
    130                 135                 140
Gly Pro Ala Arg Gly Arg Gly Arg His Pro Gly Lys Gly Val Lys Ser
145                 150                 155                 160
Pro Gly Glu Lys Ser Arg Tyr Glu Thr Ser Leu Asn Leu Thr Thr Lys
                165                 170                 175
Arg Phe Leu Glu Leu Leu Ser His Ser Ala Asp Gly Val Val Asp Leu
                180                 185                 190
Asn Trp Ala Ala Glu Val Leu Lys Val Gln Lys Arg Arg Ile Tyr Asp
            195                 200                 205
Ile Thr Asn Val Leu Glu Gly Ile Gln Leu Ile Ala Lys Lys Ser Lys
    210                 215                 220
Asn His Ile Gln Trp Leu Gly Ser His Thr Thr Val Gly Val Gly Gly
225                 230                 235                 240
Arg Leu Glu Gly Leu Thr Gln Asp Leu Arg Gln Leu Gln Glu Ser Glu
                245                 250                 255
Gln Gln Leu Asp His Leu Met Asn Ile Cys Thr Thr Gln Leu Arg Leu
            260                 265                 270
Leu Ser Glu Asp Thr Asp Ser Gln Arg Leu Ala Tyr Val Thr Cys Gln
        275                 280                 285
Asp Leu Arg Ser Ile Ala Asp Pro Ala Glu Gln Met Val Met Val Ile
    290                 295                 300
Lys Ala Pro Pro Glu Thr Gln Leu Gln Ala Val Asp Ser Ser Glu Asn
305                 310                 315                 320
Phe Gln Ile Ser Leu Lys Ser Lys Gln Gly Pro Ile Asp Val Phe Leu
                325                 330                 335
Cys Pro Glu Glu Thr Val Gly Gly Ile Ser Pro Gly Lys Thr Pro Ser
            340                 345                 350
Gln Glu Val Thr Ser Glu Glu Asn Arg Ala Thr Asp Ser Ala Thr
        355                 360                 365
Ile Val Ser Pro Pro Pro Ser Ser Pro Pro Ser Ser Leu Thr Thr Asp
    370                 375                 380
Pro Ser Gln Ser Leu Leu Ser Leu Glu Gln Glu Pro Leu Leu Ser Arg
385                 390                 395                 400
Met Gly Ser Leu Arg Ala Pro Val Asp Glu Asp Arg Leu Ser Pro Leu
            405                 410                 415
Val Ala Ala Asp Ser Leu Leu Glu His Val Arg Glu Asp Phe Ser Gly
            420                 425                 430
Leu Leu Pro Glu Glu Phe Ile Ser Leu Ser Pro Pro His Glu Ala Leu
        435                 440                 445
Asp Tyr His Phe Gly Leu Glu Glu Gly Glu Gly Ile Arg Asp Leu Phe
```

|  |  |  |
|---|---|---|
| 450 | 455 | 460 |
| Asp Cys Asp Phe Gly Asp Leu Thr Pro Leu Asp Phe | | |
| 465 | 470 | 475 |

ANTIBODIES REACTIVE WITH RETINOBLASTOMA BINDING PROTEINS AND METHODS OF USING SAME

This application is a divisional of application Ser. No. 07/979,156, filed Nov. 20, 1992.

This invention was made in part with Government support under grants issued by the National Institutes of Health Grant No. EY 05758 and Council for Tobacco Research to WHL. The Government may have certain rights in this invention.

FIELD OF THE INVENTION

This invention relates to the molecular cloning of cellular genes encoding retinoblastoma-associated proteins. In a more specific aspect it relates to the identification of a gene with properties of the transcription factor E2F.

Throughout this application various publications are referenced by partial citations within parentheses. The disclosures of these publications in their entireties are hereby incorporated by reference in this application in order to more fully describe the state of the art to which this invention pertains.

BACKGROUND OF THE INVENTION

The retinoblastoma gene (RB), the first tumor suppressor gene identified, encodes a nuclear phosphoprotein which is ubiquitously expressed in vertebrates (Friend, et al., 1986; Lee, et al., 1987b; Fung, et al., 1987). Mutations of this gene which lead to inactivation of its normal function have been found not only in 100% of retinoblastomas but also in many other adult cancers including small cell lung-carcinoma (Harbour, et al., 1988; Yokota, et al., 1988), osteosarcoma (Toguchida, et al., 1988), bladder carcinoma (Horowitz, et al., 1989), prostate carcinoma (Bookstein, et al., 1990a) and breast cancer (Lee et al., 1988). Reconstitution of a variety of RB-deficient tumor cells with wild-type RB leads to suppression of their neoplastic phenotypes including their ability to form tumors in nude mice (Huang, et al., 1988; Sumegi, et al., 1990; Bookstein, et al., 1990b; Lee, et al., 1990; Goodrich, et al., 1992; Takahashi, et al., 1991; Chen, et al., 1992). These results provide direct evidence that RB protein is an authentic tumor suppressor.

RB performs its function at the early G1/G0 phase of the cell cycle as substantiated by several observations: first, the phosphorylation of RB, presumably by members of the Cdk kinase family (Lin, et al., 1991; Lee, et al., 1991), fluctuates with the cell cycle (Chen, et al., 1989; Buchkovich, et al., 1989; DeCaprio, et al., 1989); second, the unphosphorylated form of RB is present predominantly in the G0/G1 stage (Chen, et al., 1989; DeCaprio. et al., 1989); third, microinjection of the unphosphorylated RB into cells at early G1 phase inhibits their progression into S phase (Goodrich, et al., 1991). These observations suggest that RB may serve as a critical regulator of entry into cell cycle and its inactivation in normal cells could lead to deregulated growth.

How RB functions is the subject of intense inquiry. Two known biochemical properties of the RB protein have been described; one is its intrinsic DNA binding activity which was mapped to its C-terminal 300 amino acid residues (Lee et al., 1987b; Wang, et al., 1990b); another is its ability to interact with several oncoproteins of the DNA tumor viruses (DeCaprio, et al., 1988; Whyte, et al., 1988; Dyson, et al., 1989). This interaction was mapped to two discontinuous regions at amino acids 379–545 and 575–678, designated as the T-binding domains (Hu, et al., 1990; Huang, et al., 1990).

Interestingly, mutations of the RB proteins in tumors were frequently located in these same regions (Bookstein and Lee, 1991). These results imply that the T-binding domains of RB proteins are functionally important and the interaction of RB with these oncoproteins may have profound biological significance. The identification of cellular proteins that mimic the binding of T to RB revealed a potentially complicated network. Several proteins including c-myc (Rustgi, et al., 1991), Rb-p1, p2 (Defeo-Jones, et al., 1991) and 8–10 other proteins (Kaelin, et al., 1991; Lee, et al., 1991; Huang, et al., 1991) have been shown to bind to RB in vitro.

As the foregoing demonstrates, there clearly exists a pressing need to identify and characterize the cellular affiliates of the retinoblastoma gene. The present invention satisfies this need and provides related advantages as well.

SUMMARY OF THE INVENTION

This invention provides an isolated nucleic acid molecule encoding a retinoblastoma-associated protein, and isolated proteins having transcriptional factor E2F biological activity and RB-binding activity.

This invention further provides vectors such as plasmids and viruses comprising a DNA molecule encoding a retinoblastoma-associated protein adapted for expression in a bacterial cell, a yeast cell, or a mammalian cell.

This invention provides a mammalian cell comprising a DNA molecule encoding a retinoblastoma-associated protein.

This invention provides an antibody capable of specifically binding to a retinoblastoma-associated protein. This invention also provides hybridoma cell lines that produce monoclonal antibodies and methods of using these antibodies diagnostically and prognostically.

BRIEF DESCRIPTION OF THE FIGURES

FIGS. 4A–4B show the restriction map and nucleic and amino acid sequences of Ap12. Clone A6, 2,492 nucleotides, was completely sequenced (SEQ ID Nos: 13–14). A: restriction map of Ap12 (A6) which has the longest open reading frame. G12 is the original Ap12 clone obtained by the RB-sandwich screening. A6 and B6 were isolated by rescreening of cDNA libraries. Only restriction sites used in the construction of Ap12 derivatives are shown. B: sequence of Ap12 and predicted amino acid sequence. The squares indicate the leucine repeats. Two putative Cdk phosphorylation sites are underlined.

FIG. 10 shows the partial nucleic acid sequence of clone Ap2. p=5' (SEQ ID NO: 5) sequence; r=3' (SEQ ID NO: 6) sequence.

FIG. 11 shows the partial nucleic acid sequence of clone Ap8. p=5' (SEQ ID NO: 7) sequence; r=3' (SEQ ID NO: 8) sequence.

FIG. 12 shows the partial nucleic acid sequence of clone Ap15. p=5' (SEQ ID NO: 9) sequence; r=3' (SEQ ID NO: 10) sequence.

FIG. 13 shows the full length nucleic acid sequence of clone Ap4(SEQ ID NO: 11).

FIG. 14 shows the full length nucleic acid sequence of clone Ap10(SEQ ID NO: 12).

DETAILED DESCRIPTION OF THE INVENTION

Figure 1A:
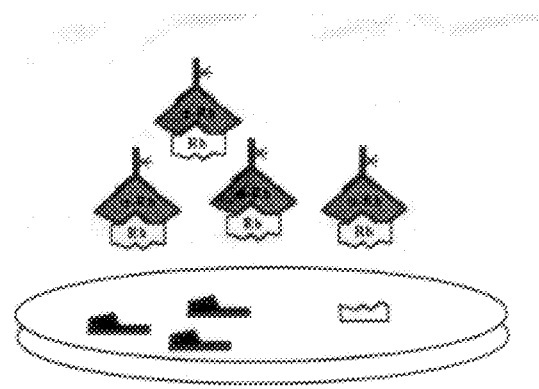
FIGS. 1A–1D show the results of RB-sandwich screening. λgt11 cDNA expression libraries were plated and screened using the RB-sandwich containing purified p56-RB, anti-RB antibody, and alkaline-phosphatase conjugated secondary antibody. A and B, a diagram of the RB-sandwich screening. C and D, hybridized filters with the RB-sandwich (left halves of the filters) in which the positive signal indicates a RbAp-RB complex (C) or T-antigen-RB complex (D). The right halves of the filters were probed with the RB-minus sandwich.
Figure 1B:
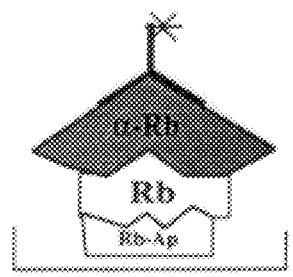
Figure 1C:
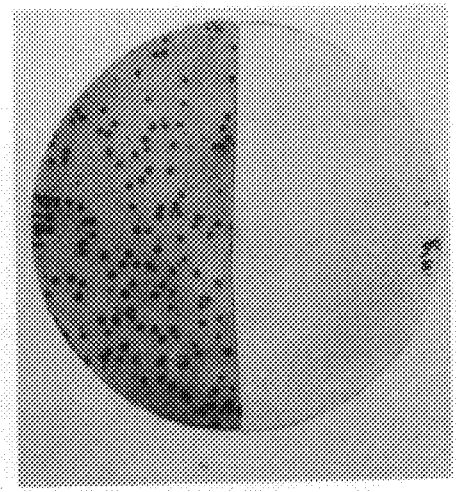
Figure 1D:
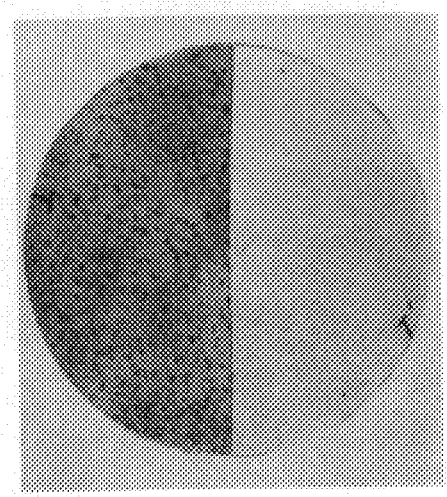

The retinoblastoma protein interacts with a number of cellular proteins to form complexes which can be crucial for its normal physiological function. To identify these proteins, nine distinct gene cDNAs were cloned by direct screening of cDNA expression libraries using purified RB protein as a probe. Preliminary characterization of these clones indicates that a majority of these genes encode novel proteins. One of them, Ap12, expresses a 2.8 Kb mRNA in a cell cycle-dependent manner.

The longest cDNA isolate of Ap12 encodes a putative protein of 476 amino acids with several features characteristic of transcription factors. The C-terminal 114 amino acids of Ap12 binds to unphosphorylated RB in regions similar to where T-antigen binds and has transactivation activity. A region near the N-terminus contains a putative leucine zipper flanked by basic residues and is capable of specifically binding to an E2F cognate sequence. Expression of Ap12 in monkey kidney CV1 cells significantly enhanced E2F-dependent transcriptional activity. Although the E2F gene has not been cloned and its identity is based solely on the ability to recognize and bind to a specific DNA sequence, these results establish that the novel clones encode proteins with known properties of the transcription factor E2F and which bind RB.

Accordingly, the present invention provides an isolated nucleic acid molecule encoding a retinoblastoma-associated protein. As used herein, the term "isolated nucleic acid molecule" refers to a nucleic acid molecule that is in a form that does not occur in nature. One means of isolating a human retinoblastoma nucleic acid molecule is to probe a human cDNA expression library with a natural or artificially designed antibody to retinoblastoma, using methods well known in the art (see Maniatis et al. (1989) which is incorporated herein by reference). DNA and cDNA molecules which encode human retinoblastoma-associated polypeptides can be used to obtain complementary genomic DNA, cDNA or RNA from human, mammalian or other animal sources. The isolated nucleic acids can also be used to screen cDNA libraries to isolate other genes encoding RB-associated proteins.

The present invention provides soluble retinoblastoma-associated polypeptides that have DNA binding and RB binding activity. For the purposes of illustration only, nucleic acid sequences encoding the polypeptides are identified in FIGS. 4A–4B and 10–14. The nucleic acid sequences encoding the soluble retinoblastoma-associated polypeptide are included within the sequences set forth in FIGS. 4A–4B and 10–14.

As used herein "retinoblastoma-associated polypeptide" means a polypeptide having DNA binding as well as an RB-binding activity. Examples of retinoblastoma-associated polypeptides substantially the same as the amino acid sequence of clone Ap12, shown in FIG. 4A–4B, or the amino acid sequence encoded by the nucleic acid sequences of clones Ap 2, 4, 8, 10 and 15, or active fragments thereof. As used herein, "an active fragment or biologically-active fragment" refers to any portion of the retinoblastoma-associated polypeptide shown in FIG. 4A–4B, or that encoded by clones Ap 2, 4, 8, 10 and 15 shown in FIGS. 10–14. Methods of determining whether a polypeptide can bind RB are well known to those of skill in the art, for example, as set forth herein.

As used herein, the term "purified" means that the molecule or compound is substantially free of contaminants normally associated with a native or natural environment. The purified polypeptides disclosed herein include soluble polypeptides. For example, the purified soluble polypeptide can be obtained from a number of methods. The methods available for the purification of proteins include precipitation, gel filtration, ion-exchange, reversed-phase, and affinity chromatography. Other well-known methods are described in Deutscher et al. *Guide to Protein Purification: Methods in Enzymology Vol.* 182, (Academic Press 1990), which is incorporated herein by reference. Alternatively, a purified polypeptide of the present invention can also be obtained by well-known recombinant methods as described, for example, in Maniatis et al., *Molecular Cloning: A Laboratory Manual* 2d ed. (Cold Spring Harbor Laboratory 1989), also incorporated herein by reference. An example of this means for preparing soluble retinoblastoma-associated polypeptide is to express nucleic acid encoding the retinoblastoma-associated polypeptide in a suitable host cell, such as a bacterial, yeast or mammalian cell, using methods well known in the art, and recovering the expressed soluble protein, again using methods well known in the art. The soluble polypeptide and biologically active fragments thereof can also be produced by chemical synthesis. Synthetic polypeptides can be produced using Applied Biosystems, Inc. Model 430A or 431A automatic polypeptide synthesizer and chemistry provided by the manufacturer. The soluble polypeptide can also be isolated directly from cells which have been transformed with the expression vectors described below in more detail.

The invention also encompasses nucleic acid molecules which differ from that of the nucleic acid molecules shown in Figures, but which produce the same phenotypic effect. These altered, but phenotypically equivalent nucleic acid molecules are referred to "equivalent nucleic acids." This invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention. As used herein, the term "nucleic acid" encompasses RNA as well as single- and double-stranded DNA and cDNA. In addition, as used herein, the term "polypeptide" encompasses any naturally occurring allelic variant thereof as well as man-made recombinant forms.

The invention further provides the isolated nucleic acid molecule operatively linked to a promoter of RNA transcription, as well as other regulatory sequences. As used herein, the term "operatively linked" means positioned in such a manner that the promoter will direct the transcription of RNA off the nucleic acid molecule. Examples of such promoters are SP6, T4 and T7. Vectors which contain both a promoter and a cloning site into which an inserted piece of DNA is operatively linked to that promoter are well known in the art. Preferable, these vectors are capable of transcribing RNA in vitro or in vivo. Examples of such vectors are the pGEM series (Promega Biotech; Madison, Wis.).

This invention provides a vector comprising this isolated nucleic acid molecule encoding a retinoblastoma-associated polypeptide. Examples of vectors are viruses, such as bacteriophages, baculoviruses and retroviruses, cosmids, plasmids and other recombination vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and anti-sense RNA. Other means are available and one well known for those of skill in the art.

Also provided are vectors comprising a DNA molecule encoding a human retinoblastoma-associated polypeptide, adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding retinoblastoma-associated polypeptide as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis et al. supra. 1989). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example the methods described above for constructing vectors in general. Expression vectors are useful to produce cells that express the polypeptide.

This invention provides a host cell, e.g. a mammalian cell, containing a nucleic acid molecule encoding a human retinoblastoma-associated polypeptide. An example is a mammalian cell comprising a plasmid adapted for expression in a mammalian cell. The plasmid has a nucleic acid molecule encoding a retinoblastoma-associated polypeptide and the regulatory elements necessary for expression of the polypeptide. Various mammalian cells may be utilized as hosts, including, for example, mouse fibroblast cell NIH3T3, CHO cells, HeLa cells, Ltk- cells, etc. Expression plasmids such as those described supra can be used to transfect mammalian cells by methods well known in the art such as calcium phosphate precipitation, DEAE-dextran, electroporation or microinjection.

Also provided are antibodies having specific reactivity with the retinoblastoma-associated polypeptides of the subject invention, such as anti-Ap12 antibody, or any antibody having specific reactivity to a retinoblastoma-associated polypeptide. Immunologically active fragments of antibodies are encompassed within the definition of "antibody." Identification of immunologically active fragments can be performed, for example, as detailed below. The antibodies of the invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The polypeptide, particularly retinoblastoma-associated polypeptide of the present invention, can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical synthesis or recombinant methods described, for example, in Maniatis et al., surra, incorporated herein by reference. The antibodies can be used for determining the presence or purification of the retinoblastoma-associated polypeptide of the present invention. With respect to the detecting of such polypeptides, the antibodies can be used for in vitro diagnostic or in vivo imaging methods for diagnosing or prognosing pathologies associated with loss of functional RB protein.

Immunological procedures useful for in vitro detection of the target retinoblastoma-associated polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

Identification of RB-associated proteins. The simplest model for RB function is that relatively few target molecules which play central roles in cellular function are regulated by the retinoblastoma protein. Inactivation of RB by any one of three means, phosphorylation (Chen, et al., 1989; DeCaprio, et al., 1989), mutations (Shew, et al., 1990) or oncoprotein perturbation (DeCaprio, et al., 1988; Goodrich, et al., 1991; Whyte, et al., 1988), could potentially uncouple RB connections and lead to deregulated growth. Until this report, there were, indeed, only a limited number of molecules that were known to be capable of interacting with RB, such as two proteins of unknown function, p1 and p2, the myc protein and 8–10 other unidentified proteins. To genetically and biochemically dissect the RB network, it is essential to identify as many of the genes encoding interactive partners of RB as possible. To maximize the cloning probability, two different approaches were undertaken. One approach was to use a two-hybrid method developed by Field and his colleagues (Fields and Sung, 1989) based on the yeast GAL4 system to select for protein-protein interaction in vivo. The other approach, described herein, was to use an RB-sandwich to screen λgt11 cDNA expression libraries. The advantage of using this one-step RB-sandwich procedure is its simplicity, directness, and the clone isolated should encode a fusion protein that would directly interact with RB in the absence of potential bridging proteins. Screening was performed using SV40 large T antigen as a positive control. A λgt11 phage expressing T antigen was constructed for this purpose and the association between RB and T can be readily detected by this method.

Using this approach, 9 clones were isolated. All the proteins encoded by these clones are located in the nucleus. This is an important criteria for any protein that could interact with RB in a biologically significant manner, since the interaction probably would occur in the nucleus (Lee, et al., 1987b).

Transcription factors as targets of regulation by the RB protein. If the cellular function of RB is to restrict entry of cells into G1 (Goodrich, et al., 1991), the genes important for G1 progression and entrance into S phase should be regulated directly or indirectly by RB. The transcription factor E2F is known to associate with RB in a cell-cycle-dependent manner (Mudryj, 1991; Shirodkar, 1992), with a tight association being prevalent in the G0/G1 stage but not in S or M phases. There are several genes including myc, DHFR, and myb that may be subject to E2F transcriptional control (Hiebert, et al., 1989; Mudryj, et al., 1990). It is reasonable to propose that RB sequesters E2F in the G0/G1 stage in an inactive conformation. Its release from the RB complex allows it to assume an active conformation that is capable of influencing its target genes through interactions with E2F DNA-binding sites and the general transcriptional machinery. An important challenge is to determine the identity of the E2F target genes and to ascertain their role in the control of the cell cycle.

There is increasing evidence to support this simple model of RB function, which is now further supported by the finding that, in the collection of 9 newly cloned RB-associated proteins, one is a known eukaryotic upstream binding factor (UBF) which recognizes and binds to the ribosomal RNA promoter, and activates transcription mediated by RNA polymerase I through cooperative interactions with SL1 (Jantzen, et al., 1990), and another, Ap12, has properties consistent with those proposed for the E2F transcription factor. The accumulation of Ap12 mRNA around six hours post stimulation with serum coincides with the pattern of expression of delayed-early growth response genes (Lau and Nathans, 1991). The maximal level of Ap12 mRNA accumulates at the G1/S boundary, establishing that it has a role in controlling cells of entry into S phase. Also, the protein binds only to unphosphorylated RB at domains similar to those bound by T. Most interestingly, Ap12 recognizes the E2F cognate sequence and transactivates the promoter carrying such specific sequence.

Ap12 encodes a putative bZIP transcription factor. From the preliminary characterization of this gene, the putative protein deduced from the longest open reading frame is 476 amino acids in length although the initiating methionine has yet to be defined. The predicted molecular weight of the putative protein is about 51 kd which is close to the 60 kd protein immunoprecipitated by the anti-Ap12 antibody. The C-terminal region of Ap12 which binds to RB protein and has a transactivation activity, is very acidic, a hallmark of the transactivation domain of several known transcription factors such as GAL4 and VP16 (Sadowski, et al., 1988; Mitchell and Tjian, 1989). The DNA binding domain appears to be located at the middle region of the protein which features a putative leucine zipper motif flanked by stretches of basic amino acids. Since Ap12 has most of the features that are characteristic of E2F, it can be considered to either encode E2F or a protein in the E2F family. Thus it is likely that E2F is also a bZIP protein which is intriguing since this is a class of transcription factors intimately involved in cell growth (e.g., fos and jun) and differentiation (e.g., C/EBP). Another hallmark of the bZIP family is a propensity to form a diverse array of heterodimeric associations among its members which adds a new layer of regulation to the control of E2F.

This vast array of possibilities presents an almost unlimited opportunity for the cell to intricately regulate the proteins involved in fine control of the cell cycle. The availability of the Ap12/E2F clone will facilitate the further elucidation of the connection between RB, E2F and cellular proliferation.

To identify the cellular affiliates of RB and to initiate the elucidation of the RB interactive cellular network, several approaches were taken to clone genes encoding RB-associated proteins. Described herein are the results from one of these approaches: screening of λgt11 expression libraries using RB as a probe. Nine distinct genes were cloned, one of which, Ap12, has characteristics which suggest that it encodes the transcription factor E2F. Clones Ap 2, 4, 8, 10, 12 and 15 all encode RB-associated proteins and are all involved in cell cycle control.

Identification of RB-associated proteins (RbAps). Two λgt11 cDNA expression libraries were constructed and screened using the purified p56-RB protein (amino acids 376–928) which includes both T-binding domains and entire C-terminal region (Lee, et al., 1991) as probe. This probe is referred to as a RB-sandwich since it contains RB protein, rabbit anti-RB antibody, (0.47) (Wang, et al., 1990a), and alkaline phosphatase conjugated goat anti-rabbit IgG. (see Materials and Methods). FIGS. 1A–1D illustrates a diagram of the sandwich screening strategy (1A and 1B). Since the association of RB and SV40 T-antigen is well documented (DeCaprio, et al., 1988), a λgt11 phage expressing T-antigen was constructed and screened using the RB-sandwich to serve as a positive control (shown in FIG. 1-D). As an example (FIG. 1-C), one of the clones' (Ap2) fusion product, was readily detected by this method. One half of each filter was used for binding to the RB-sandwich and the other half to the sandwich minus RB protein. The latter probe served as a control for the background binding due to any cross-reaction of the RB antibody or goat anti-rabbit antibody with bacterial proteins. After 5 rounds of screening of $1\times10^6$ recombinant phage, 12 clones emerged as candidate genes encoding RB-associated proteins. These clones are designated RbAp1, 2, 4, 6, 8, 9, 10, 11, 12, 13, 14, 15.

These 12 putative RbAp cDNAs were subcloned into the pGEM plasmid and a partial sequence of 500 to 600 bp from each clone was obtained. A comparison with known gene sequences present in the GENBANK database, RbAp1, 2, 4, 30 8, 10, 12, 13, 14, 15 appear to be novel genes that contain no significant homology to any known genes. However, three clones matched previously identified genes: RbAp6 is identical to nuclear lamin C (McKeon, 1986; Fisher, 1986); RbAp9 encodes a product partially homologous to the β subunits of G protein (Gullemont et al., 1989); and RbAp11 codes for the upstream binding factor (UBF) that binds to the ribosomal RNA gene promoter (Jantzen, et al., 1990). Cross-hybridization and sequencing data showed that RbAp1, 10, 13, and 14 are identical. Table 1 summarizes the preliminary characterization of all the cloned RbAps.

RbAp clones 2, 4, 8, 10, 12, and 15 are targets for RB, $p110^{RB}$, binding and all function in cell cycle control. It is possible that the retinoblastoma-associated proteins encoded by the RbAp clones are positive elements for cell proliferation. Rb binds to the protein products of these clones and, therefore, inhibits their proliferative function. As a result, the RbAp protein products cannot function positively and, therefore, are unable to promote cell cycle progression. Alterations in the RbAp ability to bind RB can result in an oncogenic effect. Assays detecting such alterations and/or mutations could determine malignancy and function as diagnostic tools for hyperproliferative diseases. Examples of hyperproliferative pathologies include, but are not limited to thyroid hyperplasia, psoriasis, Li-Fraumeni syndrome including breast cancer, sarcomas and other neoplasms, bladder cancer, colon cancer, lung cancer, benign prostatic hypertrophy and various leukemias and lymphomas. The present invention also provides antagonists of such altered and/or mutated RbAps for use in therapeutics for cancer and other hyperproliferative pathologies.

Table 1. Initial characterization of RB-associated proteins. The size of cDNA of each clone was determined by the EtBr staining of the agarose gel after digestion of the phage DNA with EcoRI. The size of mRNAs was measured by the RNA blot analysis using 28s and 18s rRNA as markers. The partial sequence from each clone was used to search GENBANK database to determine the identity of the clones. The nuclear localization was determined by immunostaining and cell fractionation (data not shown). nd=not determined.

| RbAp | Length of cDNA (kb) | Size of mRNA (kb) | in vitro Binding | Identity | Subcellular Localization |
| --- | --- | --- | --- | --- | --- |
| 1, 10, 13, 14 | 2.8 | 7.1 | + | Novel | Nucleus |
| 2 | 1.6 | 3.6 | nd | Novel | nd |
| 4 | 1.7 | 6.7 | + | Novel | Nucleus |
| 6 | 1.5 | 2.1 | + | Lamin C | Nucleus |
| 8 | 1.8 | 6.9 | nd | Novel | nd |
| 9 | 0.7 | 1.3 | + | GB-like | Nucleus & Membrane |
| 11 | 1.5 | 3.2 | + | UBF | Nucleus |
| 12 | 1.4 | 2.8 | + | Novel | nd |
| 15 | 1.5 | 6.5 | + | Novel | Nucleus |

Figure 2:
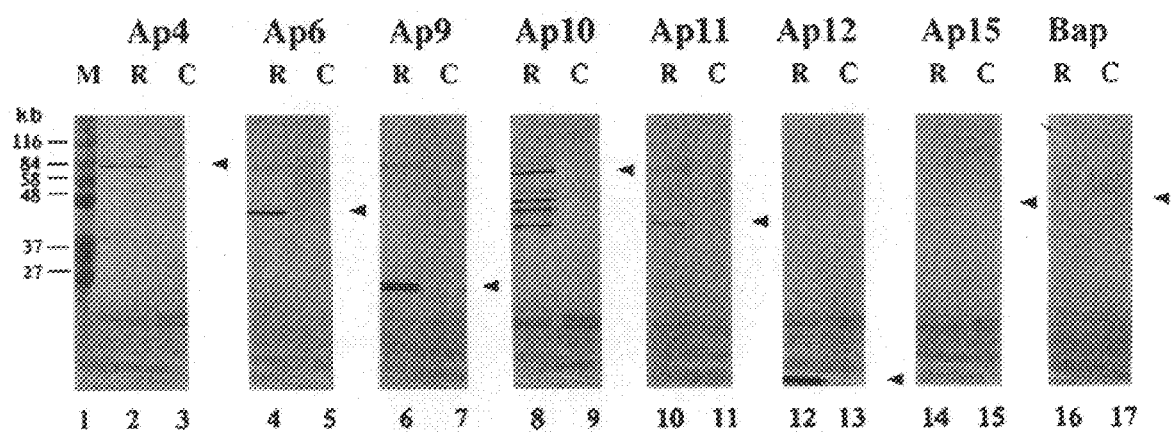
FIG. 2 shows binding of RbAps to RB in vitro. The cDNA insert from each clone (Ap4, 6, 9, 10, 11, 12, 15) was subcloned into the pFLAG plasmid and the lysates of FLAG-Ap fusion proteins were mixed with the GST-RB beads (R) or GST beads alone (C). The bound proteins were then analyzed by immunoblot using a monoclonal anti-FLAG antibody. The arrows indicate the FLAG-Aps bound to the GST-RB beads, which were detected by the anti-FLAG antibody. BAP=FLAG bacterial alkaline phosphatase fusion protein.

Binding of RbAps to RB in vitro. To confirm the association of RB protein with RbAps, the cloned cDNA inserts were subcloned into the plasmid pFLAG (IBI). This plasmid is designed for expressing Flag-fusion proteins in bacteria which can then be detected using an antibody against the Flag segment of the fusion. To facilitate the binding assay, the p56-RB was fused with the glutathione S-transferase (Gst) gene, expressed and purified by glutathione agarose chromatography (Gst-RB) (Smith and Johnson, 1988). To perform the RB-binding assay, the FLAG-Ap lysates were mixed with the Gst-RB or Gst beads alone (no RB). As an additional negative control, FLAG-BAP (bacterial alkaline phosphatase) was also mixed with the Gst and Gst-RB beads. After extensive washing, the bound fusion proteins were eluted and analyzed by Western blotting using the anti-FLAG monoclonal antibody. The results demonstrate that all RbAps examined are able to bind to the Gst-RB beads but not to the control Gst beads (FIG. 2). Among these clones, the binding affinity varied from Ap15, the weakest, to Ap12, the strongest.

Figure 3:
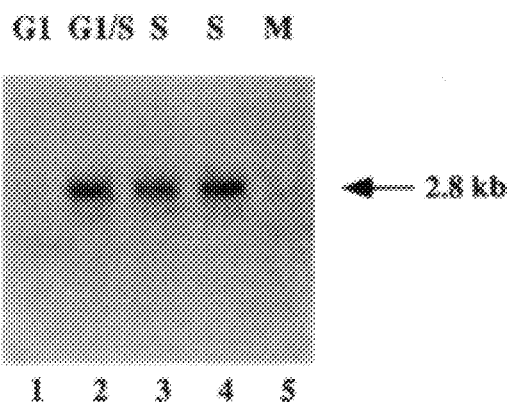
FIG. 3 shows cell cycle dependent expression of Ap12. Total RNA from CV1 cells synchronized at various stages of the cell cycle was denatured and analyzed by formaldehyde gel electrophoresis. The RNA blot was hybridized with a $^{32}$P-labeled Ap12 cDNA insert (G12). Lane 1, early G1; lane 2, G1/S boundary; lane 3, S phase (4 hours after aphidicolin release); lane 4, S phase (18 hours after replating starved cells); lane 5, M phase. The size of the mRNA (designated by an arrow) was determined by migration of the rRNA 28S and 18S, which were run on a parallel lane next to the RNA samples.

The level of Ap12 mRNA is regulated during the cell cycle. Since Ap12 consistently showed the strongest binding signal during screening, it was selected for further study. The clone has an insert of 1.4 kb with a about 1.0 kb untranslated region and an open reading frame of 114 amino acids. RNA blot analysis was performed to determine the size of the mRNA and its pattern of expression during cell cycle progression. Normal monkey kidney CV1 cells were plated in fresh medium with 10% serum in the presence of Lovastatin for 36 hours (to arrest the cell in G1 phase) (Jakobisiak, et al., 1991; Keyomarsi, et al., 1991) or aphidicolin (10 $\mu$g/ml) for 16 hours (to arrest the cells at the G1/S boundary), then released for 4 hours (to synchronize the cells in S phase) or incubated in the presence of nacodazole for another 16 hours (to allow the cells to progress to M phase) (Goodrich, et al., 1991). Total RNA from each stage was prepared for blot analysis using the Ap12 cDNA as a probe. A 2.8 kb mRNA was detected at the G1/S boundary and in S phase, but was undetectable in early G1 or M phase (FIG. 3). As a control, the expression pattern of Ap9 does not change during the cell cycle. Consistent with this observation, an increase of Ap12 mRNA expression was observed between 2 and 6 hours after serum stimulation. These findings establish that Ap12 can be involved in cell cycle progression.

Figure 4A:
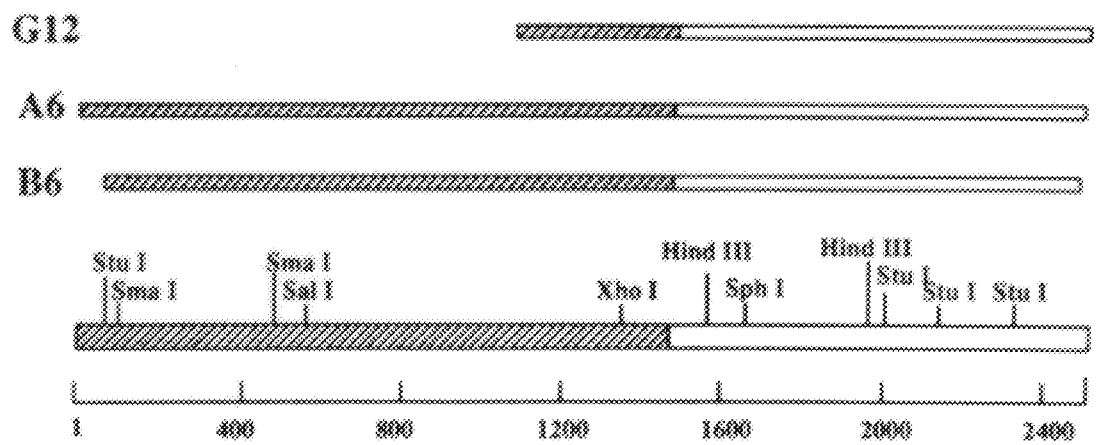
Figure 4B:
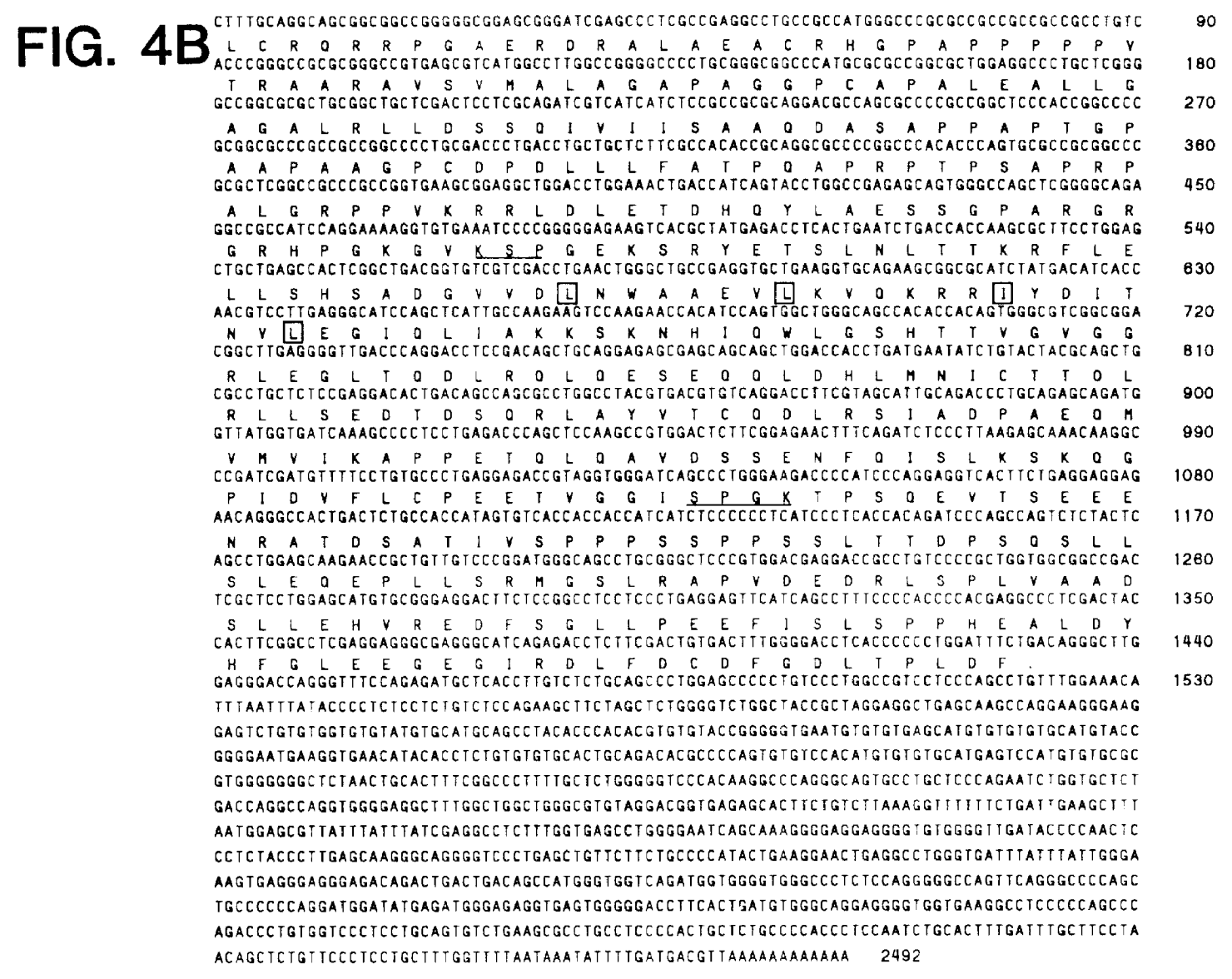

Sequence analysis of Ap12. It is apparent that the initial Ap12 cDNA clone (G12) was shorter than the size of its corresponding mRNA. The cDNA libraries were rescreened and several longer clones were isolated, among them, two clones, A6 and B6, together with the original clone (G12) were further characterized (FIGS. 4A–4B). The longest open reading frame from the 2,492 nucleotides encodes a putative protein of 476 amino acids. Distinctive features of the putative protein include the C-terminus 100 amino acids that are very acidic, and an N-terminal 43 amino acid region dominated by 15 proline residues. Following the proline-rich region are typical leucine repeats (Landschulz, et al., 1988; Vinson, et al., 1989), flanked by stretches of basic amino acids, suggesting a potential DNA-binding domain. These features are indicative of several different classes of eukaryotic transcription factors. In addition, a stretch of amino acids (LXSXE - - - DDE) (SEQ ID NO: 1) at position 389–411 resembles the sequences of T-antigen which are responsible for binding to RB protein (DeCaprio, et al., 1988). Furthermore, there are two potential phosphorylation sites for Cdk kinase (Shenoy, et al., 1989) at amino acids 159–161 (KSP) and 346–349 (SPGK) (SEQ ID NO: 2), which could modulate the function of this protein.

Figure 5A:
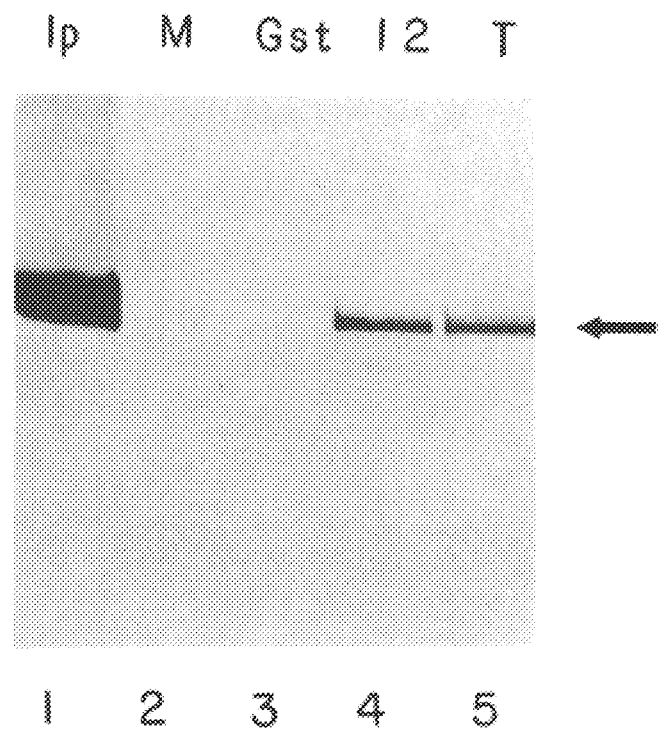
FIGS. 5A–5D show that Ap12 binds specifically to the hypophosphorylated form of RB at regions similar to T. A, Lane 1: a Molt4 lysate immunoprecipitated using a monoclonal anti-RB antibody, mAb11D7. Lane 2: molecular marker. Lanes 3–5: Molt4 cell lysates ($5 \times 10^6$ cells) were mixed with GST beads (lane 3), GST-Ap12 (lane 4) and GST-T (lane 5) beads. After washing, the RB bound to the GST fusions was analyzed by immunoblotting using a monoclonal anti-RB antibody, mAb11D7. B: a panel of RB mutant proteins expressed in a bacterial pET-T7 expression system. The T-binding domains are highlighted. C-D: the bacterially expressed wild type (pETRbc) or mutant RB proteins (pETB2, Ssp, Xs, M8, M6, M9, Nm) were mixed with the GST-Ap12 (C) or GST-T (D) beads and the bound proteins were measured by Western blot analysis using a monoclonal anti-RB antibody, mAb245.
Figure 5B:
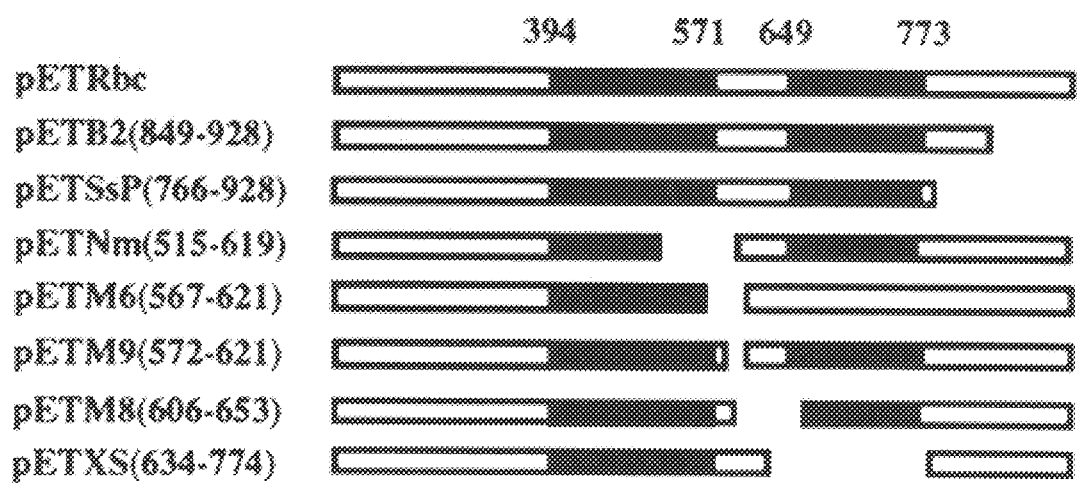
Figure 5C:
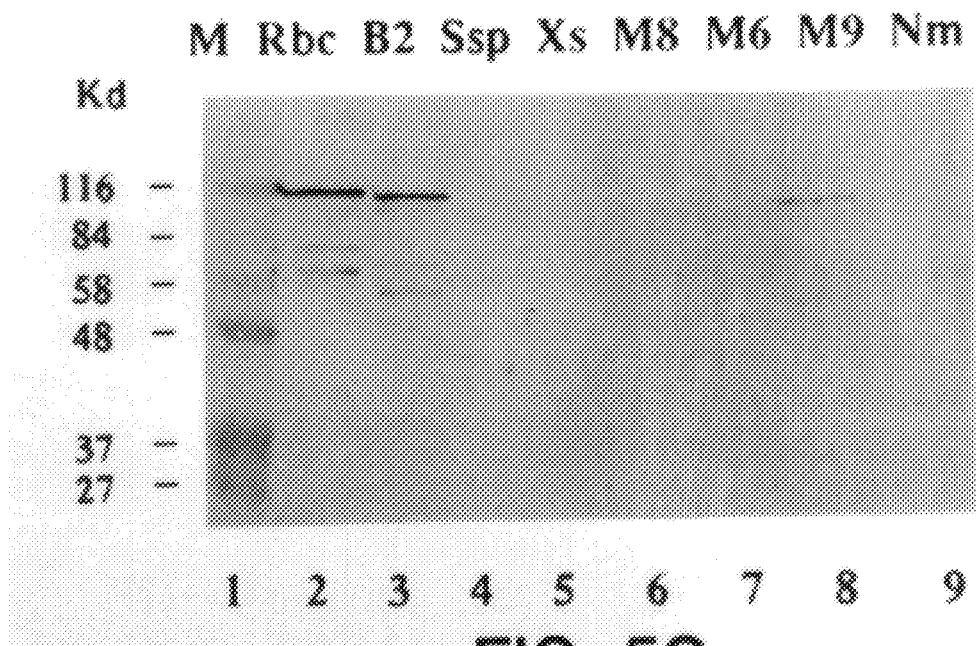
Figure 5D:
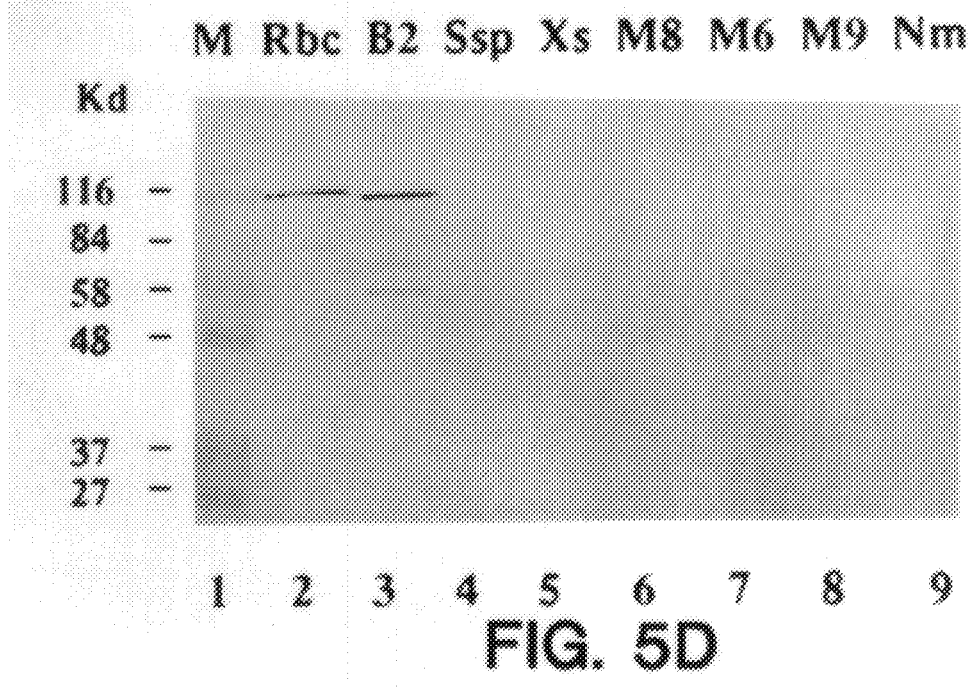

Ap12 binds only the hypophosphorylated form of RB at regions similar to those required for binding of SV40 T-antigen. To analyze the RB-binding properties of Ap12, the original clone (G12) was expressed as a Gst-fusion protein (P3) and purified by glutathione agarose chromatography. This fusion protein was used to test the binding of the Ap12 protein to full-length RB prepared from a cellular lysate of Molt4 cells, that expresses both hyper- and hypo-phosphorylated forms of the RB protein. Two additional controls were included in this experiment: one was a Gst-T-antigen fusion protein as a positive control and the other was Gst alone as negative control. As shown if FIG. 5A, the P3 protein binds only to the hypophosphorylated form and the binding affinity is very similar to that of T. Gst alone binds no detectable RB protein. To define which domain of RB is binding to Ap12, a panel of RB mutants expressed in the bacterial pET-T7 expression system (Studier et al., 1990) were mixed with the P3 beads or in parallel, with Gst-T beads. The amount of wild type or mutated RB proteins bound to the beads was determined by Western blot analysis using a monoclonal anti-RB antibody (mAb245). As shown in FIG. 5C and 5D, the mutated RB defective in binding to T also failed to bind to Ap12. These results indicate that both Ap12 and T bind to the unphosphorylated form of RB in similar regions, showing that the Ap12-RB association is biologically significant.

Figure 6A:
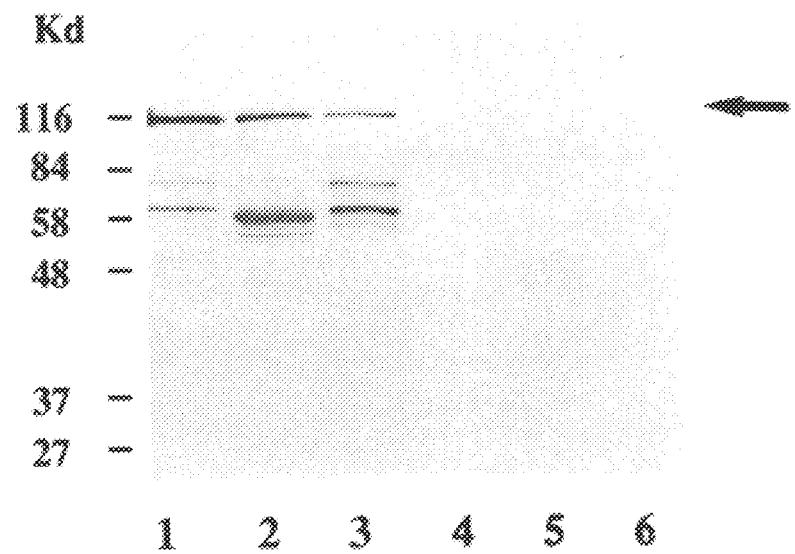
FIGS. 6A–6B show that the C-terminal region of Ap12 is required for RB-binding. A series of GST-Ap12 derivatives, P3, SH5, XH9, SX4, and XX4 were constructed (shown in panel B) and used for RB binding. The bacterially expressed pETRbc (wild type RB) was mixed with the GST-Ap12 beads and analyzed by Western blot analysis using a monoclonal anti-RB antibody, mAb245. The polypeptide encoding region for P3 is amino acids 362–476; SH5, aa 162–476; XH9, aa 1–476; SX4, aa 162–455; XX4, aa 1–455. The arrow indicates the position of p110-RB.
Figure 6B:
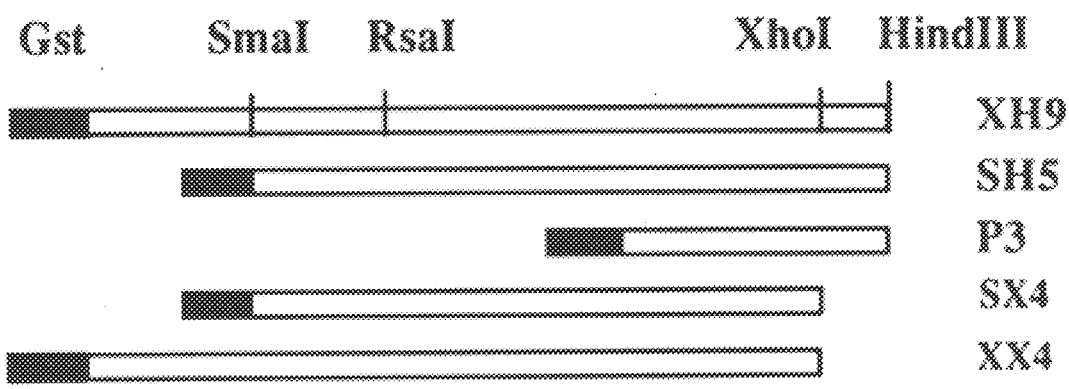

The C-terminal region of Ap12 is required for binding to RB. Since the initial P3 fusion protein which contains 114 amino acids of Ap12 binds to RB, additional experiments were designed to map the region of Ap12 required for binding to RB. Four Gst-Ap12 fusion proteins with different N-terminal or C-terminal deletions were constructed, XH9 contains the entire coding sequence of the Ap12 cDNA and SH5 (from Sma I to Hind III) contains the C-terminal 314 amino acids. XX4 and SX4 are derived from XH9 and SH5, respectively, and contain a deletion of 21 amino acids at the C-terminus. The bacterially expressed RB protein (pETRbc) was mixed with these Gst-Ap12 derivatives and analyzed by Western blotting, as described above. Xh9, SH5 and P3 bind to RB with similar affinity, suggesting that the N-terminal sequence of Ap12 contributes little to RB-binding. However, XX4 and SX4, that both have 21 amino acids deleted from the C-terminus but contain the (LXSXE - - - DDE) sequence (DeCaprio, et al., 1988; Phelps, et al., 1992), failed to bind RB (FIG. 6). Together, these results indicate that the C-terminal region of Ap12 is required for binding to RB and the (LXSXE - - - DDE) sequence alone is not sufficient for binding, suggesting that the mode of RB-Ap12 interaction may be different from that of RB-T or RB-E1A interaction.

Figure 7A:
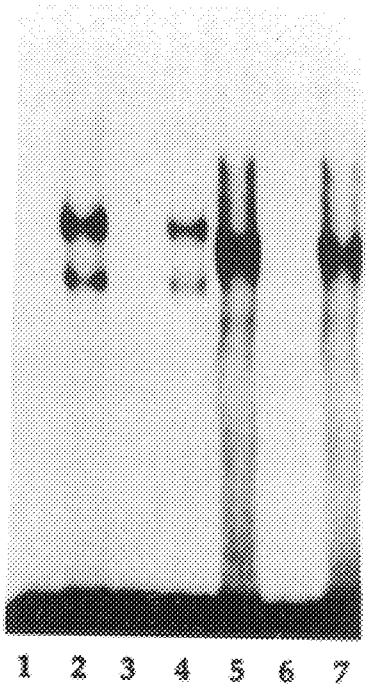
FIG. 7A–7D show that Ap12 binds specifically to the E2F recognition sequence. The lysates prepared from the bacterially expressed derivatives of GST-Ap12 (P3, SH5, XH9) and GST-Ap9, GST-Ap15 and GST alone were used for DNA mobility shift assays. The probe was a DNA fragment containing two E2F recognition sites (see Materials and Methods), which was $^{32}$P-end-labeled by Klenow fill-in reaction. A: GST-Ap2SH5 binds to the E2F-specific sequence. As a positive control, a partially purified E2F protein from HeLa cells was also used. DNA fragments containing either the wild type E2F sites or mutated E2F sites were used as competitors (See Materials and Methods). Lane 1: probe alone; Lane 2: E2F+probe; Lane 3: E2F+probe+wt competitor; Lane 4: E2F+probe+mutant competitor; Lane 5: SH5+probe; Lane 6: SH5+probe+wt competitor; Lane 7: SH5+probe+mutant competitor. B: RB interacts with the Ap12-E2F DNA complex. Lane 1: probe alone; Lane 2: SH5+probe; Lane 3: SHB+p56-RB (0.25 μg), incubate for 15 minutes, followed by probe addition; Lane 4: p56-RB+probe; Lane 5: SE5+probe; Lane 6: SH5+probe for 15 minutes, then p56-RB was added. C: DNA binding domain of Ap12 is located at a region containing a potential bZIP motif. Lane 1: P3, 200 ng; Lane 2: P3, 400 ng; Lane 3, SH5, 20 ng; Lane 4: SH5, 40 ng; Lane 5: XE9, 20 ng; Lane 6: XH9, 40 ng; Lane 7: GST alone, 200 ng; Lane 8: GST-Ap9, 200 ng; Lane 9: GST-Ap15, 200 ng.

Ap12 binds specifically to the E2F recognition sequence. Since it has been shown that RB forms a complex with the transcription factor E2F (Bagchi, et al., 1991; Bandara, et al., 1991; Chellappan, et al., 1991), and Ap12 has a potential DNA-binding domain, experiments were performed to determine whether Ap12 could interact with an E2F binding site. The bacterially expressed Gst-Ap12 (SH5) fusion protein was used in the DNA mobility shift assay of a DNA fragment containing two E2F recognition sites using previously described conditions (Yee, et al., 1989). As shown in FIG. 7A, SH5 binds that probe specifically since the complex is effectively competed with the unlabeled DNA fragment containing the wild-type E2F cognate sequence but not by a mutated sequence that differs from the wild type by only two nucleotides (Yee, et al., 1989). As a positive control, partially purified E2F protein from HeLa cells specifically binds to the DNA probe as expected.

Figure 7B:
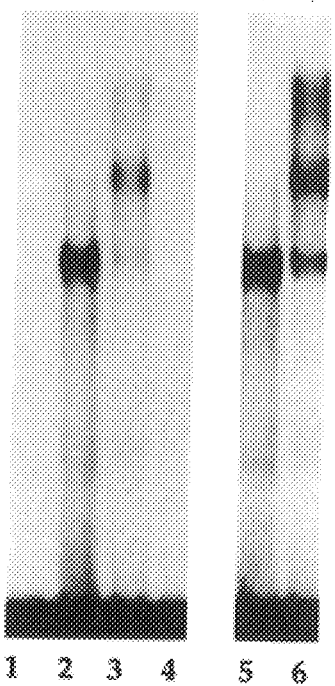

To determine if RB is able to interact with the Ap12-DNA sequence specific complex, purified p 56-RB protein was included in the DNA mobility shift assay. The experiments were performed in two ways, either SH5 was mixed with RB then added to the E2F probe (FIG. 7B, lane 3) or the fusion protein was bound to the E2F probe first followed by addition of RB (FIG. 7B, lane 6). In either case, the Ap12-DNA complex was super-shifted to more slowly migrating positions by adding RB, indicating that RB has the ability to interact with the specific Ap12-DNA complex. These results show that the Ap12 protein has a DNA-binding as well as a RB-binding activity similar to that shown for E2F.

Figure 7C:
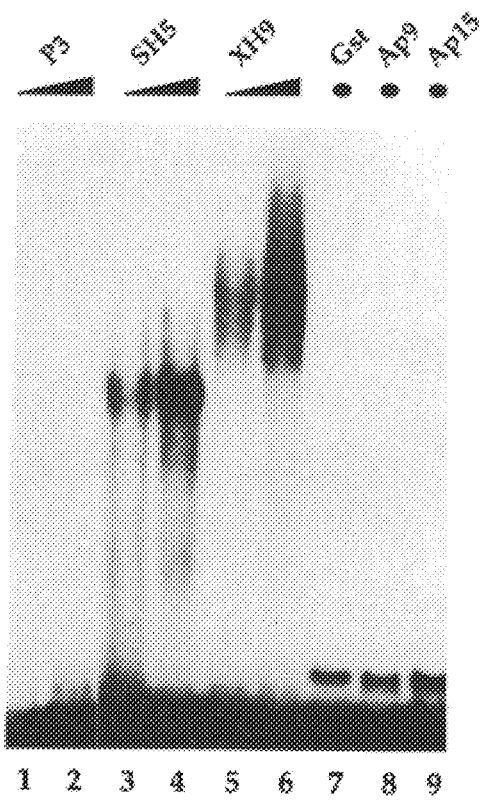
Figure 7D:
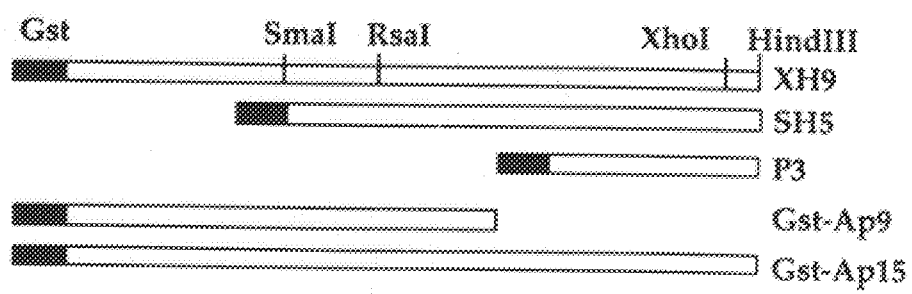

To determine whether the region containing the leucine repeats is required for DNA binding, three Gst-Ap12 fusion proteins, P3, SH5 and XH9 were chosen for DNA mobility shift assays. As shown in FIG. 7C, SH5 and XH9 which contain the putative leucine zipper and stretches of basic amino acid residues (bZIP) (Vinson et al., 1989) bound to the E2F recognition sequence whereas the C-terminal region of Ap12 (P3) did not. In addition, some other controls, Ap9, Ap15 and Gst alone, also tested negative. This result demonstrates that a region containing the putative bZIP motif is necessary for the Ap12-DNA specific interaction.

Figure 8:
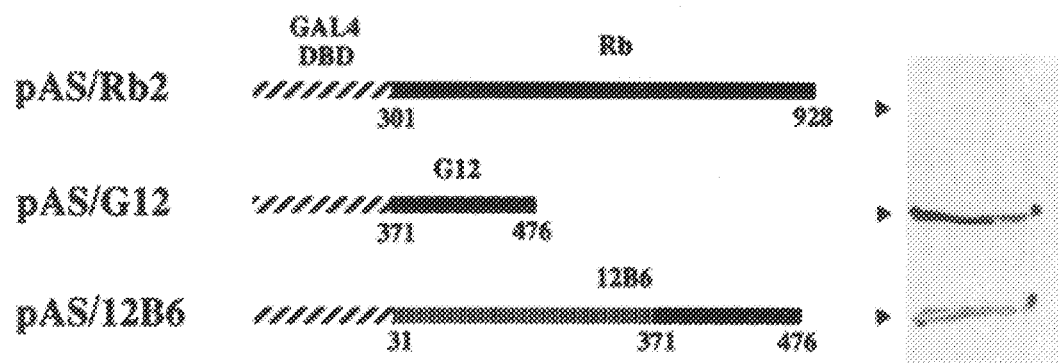
FIG. 8 shows that the C-terminus of Ap12 serves as an activation domain when fused to the GAL4 DNA binding domain in yeast. Fusion proteins of GAL4 (amino acids 1–147) and either G12 (AP12, amino acids 362–476), 12B6 (AP12, amino acids 22–476) or Rb2 (RB, amino acids 301–928) were expressed in yeast as detailed in Materials and Methods. Plasmids were used to transform Y153 to tryptophan prototropy, and single colonies of each transformation were streaked on dropout media lacking tryptophan. Following 1 day of growth at 30° C., cells were analyzed for β-galactosidase activity using a colony lift assay.

The C-terminus of AP12 can function as a transactivation domain. Highly acidic, amphipathic alpha-helical regions commonly serve as a activation domains in eukaryotic transcription factors (for review see Mitchell and Tjian, 1989). The C-terminal region of AP12 also displayed these characteristics, suggesting that it may function in an analogous manner. To test this, AP12 sequences encoding either amino acids 22–476 or the C-terminal 114 amino acids (362–476) were fused to those for the DNA binding domain of the yeast GAL4 protein (amino acids 1–147) (Keegan, et al., 1986) present on a yeast expression vector. While this GAL4 fragment can bind specifically to its recognition site ($UAS_G$) (Keegan, et al., 1986), it lacks an activation domain. Therefore, the chimeric protein relies on the fused segment to provide activation functions in order to direct transcription from a $UAS_G$ containing promoter. Several such fusions involving mammalian activators have been shown to be functional in yeast, including p53 (Fields and Jang, 1990). As shown in FIG. 8, following transformation of yeast strain harboring the E. coli lacz gene under $UAS_G$ control, both GAL4-AP12 fusions were able to activate transcription of the reporter as evidenced by β-galactosidase activity whereas the GAL4-RB control was not. This result indicates that AP12 does contain an activation domain, and that the C-terminal 114 amino acids are sufficient for this function.

Figure 9A:
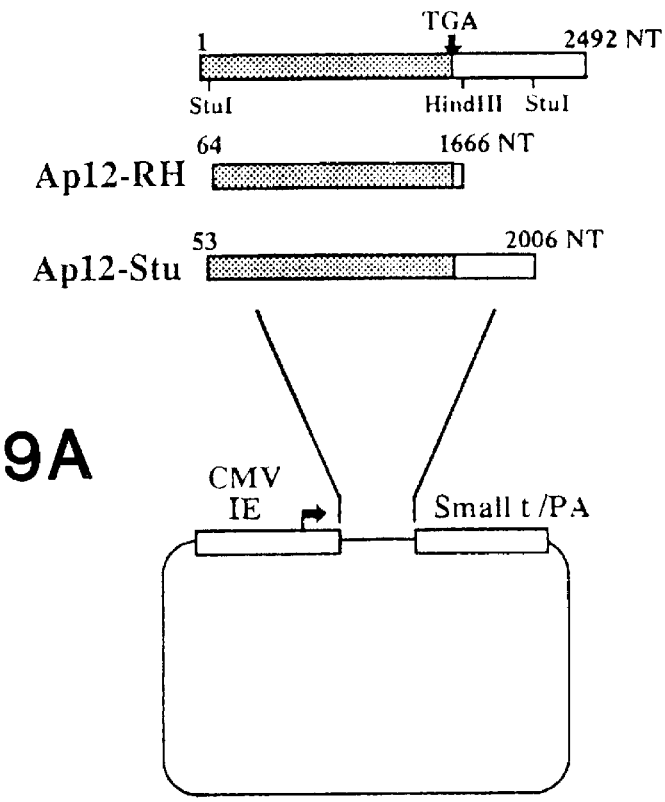
FIGS. 9A–9B show that Ap12 transactivates a promoter with E2F recognition sites. A: a diagram of the Ap12 cDNA expression vectors. PA, poly(A). B: transcriptional activation of a promoter with E2F recognition sequences. 10 μg of either pA$_{10}$CAT or pE2FA$_{10}$CAT was cotransfected with 10 μg of CMV-Ap12-Stu or CMV-Ap12-RH into monkey kidney CV1 cells. The cells were harvested after 48 hours and CAT activities were measured. CMV-E4 was cotransfected with the reporter plasmids as well as the reporter plasmids alone to serve as a control.
Figure 9B:
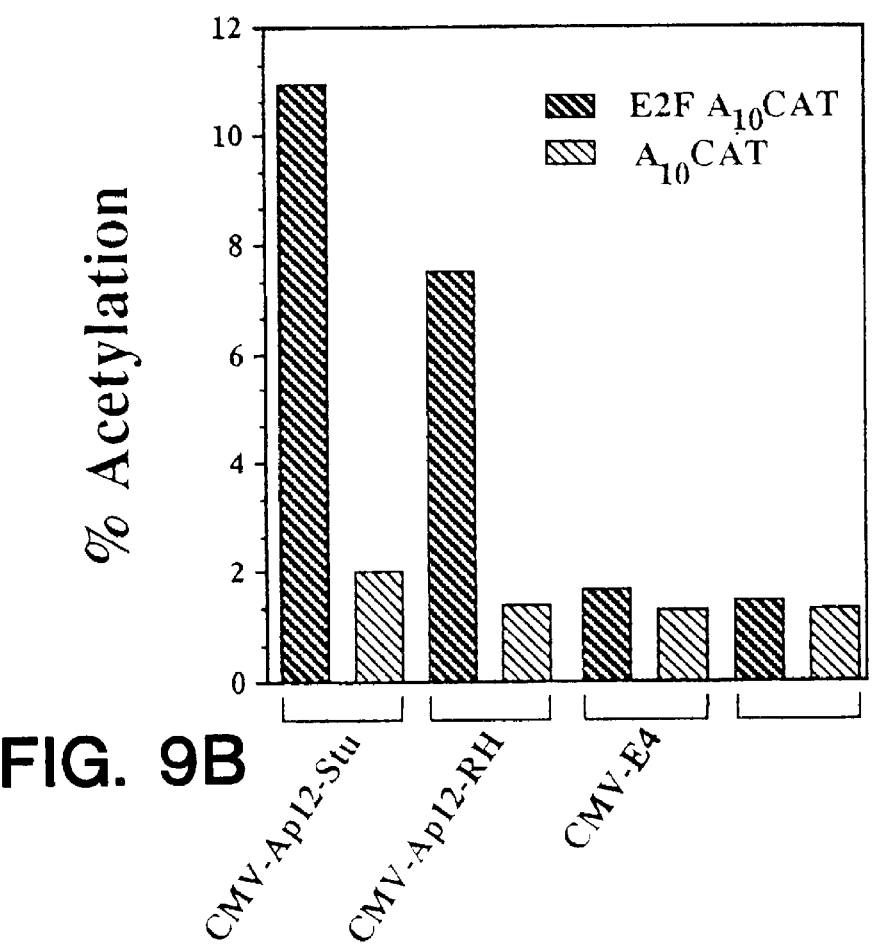

Expression of Ap12 in CV1 cells transactivates a promoter with E2F recognition sequences. To determine whether Ap12 can activate transcription in an E2F binding site-dependent manner, two plasmids, CMV-Ap12-Stu and CMV-Ap12-RH, were constructed to express the Ap12 in mammalian cells under the control of a cytomegalovirus (CMV)-IE promoter (Neill, et al., 1991) (FIG. 9A). Two reporter plasmids, $pE2FA_{10}CAT$ with two E2F sites upstream of the CAT reporter gene, and $pA_{10}CAT$ containing no E2F binding sites (Yee, et al., 1989), were used for this assay. FIG. 9B showed that the expression of either CMV-Ap12-Stu or CMV-Ap12-RH significantly enhanced CAT activity when $pE2FA_{10}CAT$, but not $pA_{10}CAT$, was cotransfected. Expression of CMV-E4 has no apparent effect when compared with the control cells which were only transfected with the reporter plasmid. These data suggested that Ap12 encodes a functional transcription factor which activates promoters with E2F recognition sequences.

Isolation of cellular genes encoding Rb-associated proteins. Two cDNA libraries were constructed from poly $A^+$ RNA isolated from HeLa cells and Saos2 cells by previously described methods (Maniatis et al., 1982). The double stranded cDNAs were size fractionated by using Sepharose C1–4B chromatography and were ligated to λgt11 arms. The size of the in vitro packaged libraries was $2.0 \times 10^7$ recombinants for HeLa cells and $1.5 \times 10^7$ for Saos2 cells with the average size of inserts being 1.6 kb. The cDNA libraries were plated on one hundred 150 mm dishes at $1–2 \times 10^4$ recombinants per dish and incubated at 42° C. until plaques just became visible (3.5 hours), and then transferred to the nitrocellulose filters saturated with IPTG (10 mM) for overnight at 37° C. The filters were denatured and renatured in 6M guanidine HCl and incubated with the RB-sandwich probe in binding buffer (25 mM Hepes, pH 7.5, 50 mM NaCl, 5mM $MgCl_2$, 5 mM DTT, 0.1% NP-40, 5% milk, 1 mg/ml BSA) for 4 hours at 4° C. The RB-sandwich was prepared by mixing 1 μg of purified bacterially expressed p56-RB (Huang et al., 1991), 100 μl of preabsorbed polyclonal anti-RB antibody (anti-RB 0.47, 1:100 dilution) and 1 μl of alkaline-phosphatase conjugated secondary antibody (1:1000 dilution) per ml of binding buffer, incubated at 4° C. for 2 hours. The RB-minus control sandwich was prepared by mixing the RB antibody and the secondary antibody and used as a control to eliminate the clones cross-reacted with the anti-RB antibody. The bound filters were then washed in TBST (20 mM Tris-HCl, pH 7.5, 150 mM NaCl, 0.05% Tween-20) 5 times, 3 minutes each and color developed in BCIP/NBP (Promega, Wis.). Positive clones from the initial screening were picked and subjected to second and third rounds of screening. The clones that consistently showed positive signals with the RB-sandwich but not with the RB-minus sandwich were then selected for fourth and fifth rounds of screening by plating at low density mixed with control phages to ensure homogenous isolates obtained which gave strong positive signals over the background.

Plasmid construction and fusion protein expression. The cDNA inserts of RbAps clones were subcloned into the pGEM1 for sequencing analysis. To express RbAp fusion proteins in vitro, the cDNA inserts were reconstructed in-frame into the pFLAG fusion protein expression system (IBI). The expression of the FLAG fusion proteins were induced by 0.2 mM of IPTG and the bacterial lysates were prepared by two rounds of freeze-and-thaw followed by sonication in lysis buffer B (50 mM Tris-HCl, pH 7.5, 100 mM NaCl, 5 mM DTT, 0.2% NP-40, 1 mM PMSF, 1 μg/ml Leupeptin, 5 μg/ml Aprotinin, 1 μg/ml Antipain) and were clarified by centrifugation. To express the RB protein in vitro, the p56 version of the RB cDNA fragment (aa 377–928) was subcloned into a plasmid expressing glutathione S-transferase (GST) fusion protein pGEX-2T (Smith and Johnson, 1988) and the bacterially expressed GST-RB fusion was prepared and purified using GST agarose beads.

In vitro binding assay. Bacterial lysates (100 μl) containing about 0.5 μg of the FLAG-RbAps were mixed with 20 μl of the GST-RB beads or GST beads carrying 1–2 μg of the fusion protein in 400 μl lysis buffer B at 4° C. for 60 minutes. The bound beads were subsequently washed 5 times in 1 ml PBS/0.2%NP-40 and the protein complex was boiled in SDS loading buffer. The bound FLAG fusion proteins were then analyzed by SDS polyacrylamide gel electrophoresis, immunoblotted and probed with an anti-FLAG monoclonal antibody (IBI).

Construction of mutated RB proteins expressed in the bacterial pET-T7 system. In addition to pETRbc, pETM6 and pETM9 (Huang et al., 1991), pETB2, pETSsp and pETM8 were constructed by cloning AhaII-BamHI fragments from pB2, pSsp and pM8 (Huang et al., 1990) into the corresponding pET expression vector. The bacterial lysates were prepared as described in previous section.

Construction of GST-RbAp12 fusion proteins. The DNA fragments derived from RbAp12 clones were subcloned into the GST fusion plasmids. GST-P3 was constructed by cloning the Eco RI-Sph I fragment from the original C-terminal 1.3 kb cDNA (G12) into the pGEPK (Chen, unpublished), a derivative from pGEX-2T (Smith, 1988). GST-SH5 contains the SmaI-HindIII fragment from clone B6 and GST-XH9 contains the EcoRI-HindIII fragment of clone A6 that contains the entire coding sequence. GST-SX4 and GST-XX4 are derived from GST-SH5 and GST-XH9, respectively, but the C-terminal XhoI-HindIII fragment is deleted.

RNA Blot Analysis. Total RNA extracted by the guanidine isothiocyanate-CsCl method (Maniatis et al., 1982) was denatured in 50% formamide, 2.2M formaldehyde, 20 mM Na borate (pH 8.3) and analyzed by 1.0% agarose gel electrophoresis. The RNA was then transferred to Hybond paper (Amersham) and the blot was immobilized by UV crosslinking. Prehybridization and hybridization were carried out in 50% formamide, 5×SSPE, 5×Denhardt's, 1% SDS and 100 µg/ml salmon sperm DNA and hybridization was performed in presence of $^{32}$P-labeled 1.3 kb RbAp12 insert DNA at 45° C. for 18 hours. The initial washing was carried out in 2×SSC, 0.1% SDS at room temperature and the final washing was in 0.1×SSC, 0.1% SDS at 65° C. for 45 minutes.

DNA gel mobility shift assay. The insert from plasmid containing two E2F recognition sequences (TTTCGCGC - - - GCGCGAAA) (SEQ ID NO: 3) was used as a probe for the gel mobility shift assay and also served as a competitor. A plasmid containing a mutated E2F site (TTTAGCGC - - - GCGCTAAA) (SEQ ID NO: 4) (Huang et al., 1992), which does not bind to E2F, was also used as a competitor. The assay was performed as described previously (Yee et al., 1989). The diluted GST-Ap12 bacterial lysates (20 ng for SH5 and XH9 fusion proteins, 200 ng for P3, Gst, GstAp9 and GstAp15) were incubated with 1×binding buffer (20 mM Hepes, pH 7.6, 1 mM MgCl$_2$, 0.1 mM EGTA, 40 mM KCl, 10% glycerol), 0.1% NP40, 1 mg/ml salmon sperm DNA at room temperature for 15 minutes and the $^{32}$p-end-labeled (Klenow fill-in) probe was added for another 30 minutes. The protein-DNA complexes were analyzed by 4% acrylamide gel electrophoresis in 0.25×TBE buffer at 4° C.

Yeast Expression Vector and Strain. The expression plasmid used in yeast was based on the pAS1 vector. Briefly, the plasmid contains the ADH1 promoter driving expression of the GAL4 DNA-binding domain followed by a downstream polylinker. The vector also carries the 2µ origin and TRP1 gene for maintenance and selection in yeast. pAS/G12 was constructed by subcloning the EcoRI fragment isolated from G12 into the unique EcoRI site in pAS1. Similarly, pAS/12B6 was built using the EcoRI fragment from p12B6 and subcloning into the pAS1 EcoRI site. pASRb2 will be described elsewhere (Durfee et al., unpublished). The Saccharomyces cerevisiae strain used was Y153 (MATa, trp-901, leu2-3, -112, ade2-101, ura3–52::URA3 (GAL1-1acZ), MEL (GAL1-1acZ); (Durfee et al., unpublished).

Yeast Transformation and β-galactosidase Assay. Yeast transformation was carried out using the LiOAc method as described previously (Schiestl and Gietz, 1989). After transformation, cells were plated on synthetic dropout media lacking tryptophan to select for the presence of the plasmid. Following 2–3 days growth at 30° C., single colonies from each transformation were streaked onto another selective plate and allowed to grow an additional 24 hours. The colony color β-galactosidase activity assay was then performed as described (Breeden and Nasmyth, 1985) except the nitrocellulose filters were submerged in liquid nitrogen for about 30s–60s to permeabilize the cells, then thawed at room temperature before overlaying on Whatman filters saturated with LacZ-X-Gal solution (Breeden and Nasmyth, 1985). The color developed in about 20 minutes in the case of the AP12 clones. No color change was observed with the pAS/Rb2 clone even after overnight exposure.

Transient Transfection Assay. The transfections were carried out with CV1 cells by conventional calcium phosphate precipitation method. The plasmid pCMVAp12Stu was constructed by cloning the StuI fragment from clone A6 into the SmaI site of pCMV and plasmid pCMVAp12RH contains the EcoRI-HindIII fragment of clone B6. The plasmid pCMVE4 was used as a control. The CMV constructs were cotransfected with plasmids pE2FA$_{10}$CAT (containing two E2F binding sites) and PA$_{10}$CAT (containing no E2F binding sites) with the same number of cells (5×10$^6$) and the CAT activities were measured after 48 hours as described previously (Gorman et al., 1982).

Although the invention has been described with reference to the presently preferred embodiments, it should be understood that various modifications can be made without departing from the spirit of the invention. Accordingly, the invention is limited only by the claims which follow.

REFERENCES

Bagchi, S., Weinmann, R. and Raychaucdhuri, P. (1991). The retinoblastoma protein copurifies with E2F-I, an E1A-regulated inhibitor of the transcription factor E2F. Cell 65, 1063–1072.

Bandara, L. R., Adamczewski, J. P., Hunt, T. and LaThangue, N. B. (1991). Cyclin A and the retinoblastoma gene product complex with a common transcription factor. Nature. 352, 249–251.

Bookstein, R. and Lee, W.-H. (1991). Molecular genetic of the retinoblastoma suppressor gene. CRC Crit. Rev. Oncogenesis. 2, 211–227.

Bookstein, R., Rio, P., Madreperia, S., Hong, F., Allred, C, Grizzie, W. E. and Lee, W.-H. (1990a). Promoter deletion and loss of retinoblastoma gene expression in human prostate carcinoma. Proc. Natl. Acad. Sci. U S A. 87:7762–7766

Bookstein, R., Shew, J.-Y., Chen, P.-L, Scully, P. and Lee, W.-H. (1990b). Suppression of tumorigenicity of human prostate carcinoma cells by replacing a mutated RB gene. Science 247,712–715.

Breeden, L. and Nasmyth, K. (1985). Regulation of the yeast HO gene. Cold Spring Harbor Symp. Quant. Biol.50, 643–650.

Buchkovich, K, Duffy, L. A. and Harlow, E. (1989).The retinoblastoma protein is phosphorylated during specific phase of the cell cycle. Cell. 58, 1097–1105.

Chellappan, S. P., Hiebert, S., Mudryj, M., Horowitz, J. M. and Nevins, J. R. (1991). The E2F transcription factor is a cellular target for the RB protein. Cell. 65, 1053–1061.

Chen, P.-L, Chen, Y., Shan, B., Bookstein, R., Lee, W-H. (1992). Stability of RB expression determines the tumorigenicity of reconstituted retinoblastoma Cells. Cell Growth Diff. 3,119–125.

Chen, P.-L., Scully, P., Shew, J.-Y., Wang, J. Y.-J. and Lee, W.-H. (1989). phosphorylation of the retinoblastoma gene product is modulated during the cell cycle and cellular differentiation. Cell. 58, 1193–1198.

DeCaprio, J. A., Ludlow, J. W., Figge, J., Shew, J.-Y., Huang, C.-M., Lee, W.-H., Marsillo, E., Paucha, E. and Livingston, D. M. (1988). SV40 large tumor antigen forms a specific complex with the product of the retinoblastoma susceptibility gene. Cell.54, 275–283.

DeCarrio, J. A, Ludlow, J. W., Lynch, D., Furukawa, Y., Griffin, J., Pawnica-Worms, H., Huang, C.-M. and Livingston, D. M. (1989). The product of the retinoblastoma susceptibility gene has properties of a cell cycle regulatory element Cell.58,1085–1095.

Defeo-jones, D., Huang, P. S., Jones, R. E., Haskell, K. M., Vuocolo, G. A., Hanobik, M. G., Huber, H. E. and Oliff, A. (1991). Cloning of cDNAs for cellular proteins that bind to the retinoblastoma gene product. Nature. 352, 251–254.

Dyson, N., Howley, P. M., Munger, K. and Harlow, E. (1989). The human papilloma virus-16 E7 oncoprotein is able to bind to the retinoblastoma gene product. Science. 243, 934–937.

Fields, S., Jang, S. K. (1990). Presence of a potent transcription activating sequence in the p53 protein. Science. 249, 1046–1051.

Fields, S. and Sung, O-K. (1989). A novel genetic system to detect protein-protein interactions. Nature. 340, 245–246.

Fisher, D. Z. Chaudhary, N., Biobel, G. (1986). cDNA sequencing of nuclear lamins A and C reveals primary and secondary structural homology to intermediate filament protein Proc. Natl. Acad. Sci. USA. 83, 6450–4454

Friend, S. H., Bernards R., Rogelj, S., Weinberg, R. A., Rapaport, J. M., Albert, D. M. and Dryja, T. P. (1986). A human DNA segment with properties of the gene that predisposes to retinoblastoma and osteosarcoma. Nature (London). 323, 643–646.

Fung, Y. K. T., Murphree, A. L., Tang, A., Qian, J., Hinrichs, S. H. and Benedict, W. F. (1987). Structural evidence for the authenticity of the human retinoblastoma gene. Science. 236, 1657–1661.

Goodrich, D. W., Chen, Y., Scully, P. and Lee, W.-H. (1992). Expression of the retinoblastoma gene product in bladder carcinoma cells associates with a low frequency of tumor formation. Can. Res. 52, 1968–1973.

Goodrich, D. W., Wang, N. P., Qian, Y.-W., Lee, E. Y.-H. P. and Lee, W.-H (1991). The. retinoblastoma gene product regulates progression through the G1 phase of the cell cycle. Cell. 67, 293–302

Gorman, C. M., Moffat, L. F., Howard, B. H. (1982). Recombinant genomes which express chloramphenicol acetyltransferase in mammalian cells. Mol. Cell. Biol. 2, 1044–1051.

Gullemont, F., Billault, A., Auffray, C. (1989). Physical linkage of guanine nucleotide-binding protein-related gene to the chicken major histocompatibity complex. Proc. Natl. Acad. Sci. USA. 86, 4594–4598.

Harbour, J. W., Lai, S.-H., Whang-Peng, J., Gazdar, A. F., Minna, J. D. and Kaye, F. J. (1988). Abnormalities in structure and expression of the human retinoblastoma gene in SCLC. Science. 241; 353–357.

Hiebert, S. W., Lipp, M., Nevins, J. R. (1989). E1A-dependent trans-activation of the human MYC promoter is mediated by the E2F factor. Proc. Natl. Acad. Sci. U S A.86, 3594–3598.

Horowitz, J. M., Yandell, D. W., Park, S. H., Canning, S., Whyte, P., Buchkovich, K., Harlow, E., Weinberg, R. and Dryja, T. (1989). Point mutational inactivation of the retinoblastoma antioncogene. Science. 243, 937–940.

Hu, Q., Dyson, N. and Harlow, E. (1990). The regions of the retinoblastoma protein needed for binding to adenovirus E1A or SV40 T antigen are common sites for mutations. EMBO J. 9,1147–1155.

Huang, H.-J. S., Yee, J.-K, Shew, J.-Y., Chen, P.-L., Bookstein, R., Friedmann, T., Lee, E. Y.-H, P . and Lee, W.-H. (1988). Suppression of the neoplastic phenotype by replacement of the retinoblastoma gene product in human cancer cells. Science. 242, 1563–1566.

Huang, S. Shin, E., Sheppard, K-A., Chokroverty, L., Shan, B., Qian, Y-W., Lee, E Y-H P., Yee, A S. (1992). The retinoblastoma protein region required for interaction with the E2F transcription factor includes the T/E1A binding and C-terminal sequences. DNA and Cell. Biology. in press.

Huang, S., Lee, W.-H. and Lee, E. Y.-H. P. (1991). Identification of a cellular protein that competes with SV40 T antigen for binding to the retinoblastoma gene product. Nature. 160–162.

Huang, S., Wang, N.-P., Tseng , B. Y., Lee , W.-H. and Lee, E. Y.-H. P. (1990). Two distinct and frequently mutated regions of retinoblastoma protein are required for binding to SV40 T antigen EMBO J. 9, 1815–1822.

Jakobisiak, M., Bruno, S., Skierski, J. S. and Darzynkiewicz, Z. (1991). Cell. cycle-specific effects of lovastatin Proc. Nat. Acad. Sci. USA. 88, 3628–3632.

Jantzen, H.-M., Admon, A., Bell, S. P., Tjian, R. (1990). Nucleolar transcription factor hUBF contains a DNA-binding motif with homology to HMG proteins. Nature. 344, 830–836.

Kaelin, W. G. J. Pallas, D. C., DeCaprio, J. A., Kaye, F. J. and Livingston, D. M. (1991). Identification of cellular proteins that can interact specifically with the T/E1A-binding region of the retinoblastoma gene product Cell. 64, 521–532

Keegan, L., Gill, G. and Ptashne, M. (1986). Separation or DNA binding from the transcription-activating function of a eukaryotic regulatory protein. Science 231, 699–704.

Keyomarsi, K., Sandoval, L., Band, V. and Pardee, A. B. (1991). Synchronization of tumor and normal cells from G1 to multiple cell cycles by lovastatin. Can. Res. 51, 3602–3609.

Landschulz, W. H., Johnson, P. F., McKnight, S. L. (1988). The leucine zipper: a hypothetical structure common to a new class of DNA binding proteins. Science. 240, 1739–1764.

Lau, L. F., Nathans, D. (1991). Genes induced by serum growth factors. The Hormonal control regulation of gene transcription ed. P. Cohen & J. G. Foulkes. Elsevier Science Publishers. pp257–293.

Lee, E. Y.-H. P., To, H., Shew, J.-Y., Bookstein, R, Scully, P. and Lee, W.-H. (1988). Inactivation of the retinoblastoma susceptibility gene in human breast cancers. Science 241, 218–221.

Lee, W.-H., Hollingsworth, R. E., Qian, Y-W., Chen, P-L. , Hong, F., Lee, EY-HP. (1991). The RB Protein as a Cellular 'Corral' for Growth-Promoting Proteins. Cold Spring Harbor Symp. Quanti. Biol. : Cell. Cycle. 61, 211–217.

Lee, W.-H., Bookstein, R., Hong, F., Young, L.-J., Shew, J.-Y. and Lee, E. Y.-H. P. (1987a). Human retinoblastoma susceptibility gene: cloning, identification, and sequence. Science. 235, 1394–1399.

Lee, W.-H., Shew, J.-Y., Hong, F., Sery, T., Donoso, L. A., Young, L. J., Bookstein, R. and Lee, E. Y.-H. P. (1987b). The retinoblastoma susceptibility gene product is a nuclear phosphoprotein associated with DNA binding activity. Nature. 329, 642–645.

Lees, J. A., Buchkovich, K. J., Marshak, D. R., Anderson, C. W. and Harlow, E. (1991). The retinoblastoma protein is phosphorylated on multiple sites by human cdc2. EMBO J. 10, 4279–4290.

Lin, B. T., Gruenwald, S., Morla, A. O., Lee, W.-H. and Wang, J. Y. (991). Retinoblastoma cancer Suppressor gene product is a substrate of the cell cycle regulator cdc2 kinase. EMBO J. 10, 857–864.

McKeon, F., Kirschner, M., Caput, D. (1986). Homologies in both primary and secondary structure between nuclear envelope and intermediate filament proteins. Nature. 319, 463–468.

Mitchell, P. J. and Tjian, R. (1989), Transcriptional regulation in mammalian cells by sequence-specific DNA binding proteins. Science. 245, 371–378.

Mudryj, M., Hiebert, S. W., Nevins J. R. (1990). A role for the adenovirus inducible E2F transcription factor in a proliferation dependent signal transduction pathway. EMBO J. 9, 2179–2184.

Mudryj, M., Devoto, S. H., Hiebert, S. W., Hunter, T., Pines, J., Nevins, J. R. (1991). Cell cycle regulation of the E2F transcription factor involves an interaction with cyclin A. Cell. 28, 1243–1253.

Neill, S. D., Nevins, J. R. (1991). Genetic analysis of the adenovirus E4 6/7 trans activator: interaction with E2F and induction of a stable DNA-protein complex are critical for activity. J. Virol. 65, 5364–5373.

Phelps, W. C. Munger, K., Yee, C. L., Barnes, J. A., Howley, P. M. (1992). Structure- function analysis of the human papillomavirus type 16 E7 oncoprotein. J. Virol 66, 2418–2427.

Rustgi, A. K., Dyson, N. and Bernards, R. (1991). Amino-terminal domains of c-myc. and N-myc proteins mediate binding to the retinoblastoma gene product. Nature. 352, 541–544.

Sadowski, L, Ma. J., Triezenberg, S., Ptashne, M. (1988). GAL4-VP16 is an unusually potent transcriptional activator. Nature. 335, 563–564.

Schiestl, R. H. and Gietz, R. D. (1989). High efficiency transformation of intact yeast cells using single stranded nucleic acids as a carrier. Curr. Genet. 16, 339–346.

Shenoy, S., Choi, J.-K., Bagrodia, S., Copeland, T. D., Maller, J. L. and Shalloway, D. (1989). Purified maturation promoting factor phosphorylates pp60c-src at the sites phosphorylated during fibroblast mitosis. Cell. 57, 763–774.

Shew, J.-Y., Lin, B., Chen, P. L., Tseng, B. Y., Yang-Feng, T. L. and Lee, W.-H. (1990). C-terminal truncation of the RB protein leads to functional inactivation. Proc. Natl. Acad. Sci. U.S.A. 87,6–10.

Shirodkar, S., Ewen, M., Decaprio, J. A., Morgan, J., Livingston, D. M., Chittenden, T. (1992). The transcription factor E2F interacts with the retinoblastoma product and a p107-cyclin A complex in a cell cycle-regulated manner. Cell. 68,157–166.

Smith, D. B., Johnson, K. S. (1988). Single-step purification of polypeptides expressed in *E. coli* as fusions with glutathione S-transferase. Gene. 67, 31–40.

Studier, F. W., Rosenberg, A. H., Dunn, J. J., Dubendorff, J. W. (1990). Use of T7RNA polymerase to direct expression of cloned genes. Methods in Enzymology. 185, 60–89.

Sumegi, J., Uzvolgyi, E. and Klein, G. (1990). Expression of the RB gene under the control of MuLV-LTR suppresses tumorigenicity of WERI-Rb-27 retinoblastoma cells in immunodefective mice. Cell Growth Differ. 1, 247–250.

Takahashi, R. Hashimoto, T., Hong-Ji, X., Hu, S.-X, Matsui, T., Miki, T., Bigo-Marshall, H., Aaronson, S. A. and Benedict, W. F. (1991). The retinoblastoma gene functions as a growth and tumor suppressor in human bladder carcinoma cells. Proc. Nat. Acad. Sci. USA. 88, 5257–5261.

Toguchida, J., Ishizaki, K., Sasaki, M. S., Ikenaga, M., Sugimoto, M., Kotoura, Y. and Yamamuro, T. (1988). Chromosomal-reorganization for the expression of recessive mutation of retinoblastoma susceptibility gene in the development of osteosarcoma. Cancer Res. 48,3939–943.

Vinson, C. R., Sigler, P. B., McKnight, S. L. (1989). Scissors-Grip Model for DNA recognition by a family of leucine zipper proteins. Science 246, 911–916.

Wang, N.-P., Chen, P.-L., Huang, S., Donoso, L. A., Lee, W.-H. and Lee, E. Y.-H. P. (1990a). DNA-binding activity of retinoblastoma protein is intrinsic to its carboxyl-terminal region. Cell Growth Diff. 1, 233–239.

Wang, N. P., Qian, Y., Chung, A. E., Lee, W.-H. and Lee, E. Y.-H P. (1990b). Expression of the human retinoblastoma gene product pp110RB in insect cells using the baculovirus system. Cell Growth Diff. 1, 429–437.

Whyte, P., Buchkovich, K. J., Horowitz, J. M., Friend, S. H., Raybuck, M., Weinbierg, R. A. and Harlow, E. (1988). Association between an oncogene and an anti-oncogene: the adenovirus E1A proteins bind to the retinoblastoma gene product Nature. 334, 124–129.

Yee, A. S., Raychaudhuri, P., Jakoi, L., Nevins, J. R. (1989). The adenovirus-inducible factor E2F stimulates transcription after specific DNA binding. Mol. Cell Biol. 9, 598–585.

Yokota, J., Akiyama, T., Fung, Y.-K. T., Benedict, W. F., Namba, Y., Hanaoka, M., Wada, M., Terasaki, T., Shimosato, Y., Sugimura, T. and Terada, M. (1988). Altered expression of the retinoblastoma (RB) gene in small cell carcinoma of the lung. Oncogene. 3, 471–475.

---

We claim:

1. An antibody specifically reactive with a nuclear retinoblastoma-associated polypeptide, wherein the polypeptide binds to the protein product of the retinoblastoma gene.

2. The antibody of claim 1, wherein the nuclear retinoblastoma-associated polypeptide is a polypeptide selected from the group consisting of Ap1, Ap4, and Ap15, wherein Ap1 comprises a polypeptide encoded by a nucleic acid having SEQ ID NO. 12, Ap4 comprises a polypeptide encoded by a nucleic acid having SEQ ID NO. 11, and Ap15 comprises a polypeptide encoded by a nucleic acid having SEQ ID NO. 8 or SEQ ID NO. 9.

3. An antibody specifically reactive with a nuclear retinoblastoma-associated polypeptide having transcription factor E2F biological activity.

4. The antibody of claim 3, wherein the polypeptide comprises a polypeptide encoded by a nucleic acid having SEQ ID NO. 13.

5. A method for detecting a nuclear polypeptide having transcription factor E2F biological activity in a sample comprising: a. contacting the antibody of claim 3 with the sample under conditions permitting formation of antibody-antigen complex; b. detecting the presence of any complex so formed; and c. the presence of complex indicating the presence of a nuclear polypeptide having transcription factor E2F biological activity in the sample.

6. A method for detecting a nuclear polypeptide, wherein the polypeptide binds to the protein product of the retinoblastoma gene in a sample comprising: a. contacting the antibody of claim 1 with the sample under conditions permitting formation of antibody-antigen complex; b. detecting the presence of any complex so formed; and c. the presence of complex indicating the presence of a nuclear polypeptide, wherein the polypeptide binds to the protein product of the retinoblastoma gene in the sample.

7. An antibody specifically reactive to the nuclear retinoblastoma-associated polypeptide Ap1, wherein Ap1 comprises a polypeptide encoded by a nucleic acid having SEQ ID NO. 12.

8. An immunologically-reactive fragment of the antibody of claim 7.

9. The antibody of claim 7, wherein the antibody is a monoclonal antibody.

10. The antibody of claim 7, wherein the antibody is labeled with a detectable marker.

11. A hybridoma cell line producing the antibody of claim 7.

12. A method for detecting the nuclear retinoblastoma-associated polypeptide Ap1 in a sample suspected of containing such protein, wherein Ap1 comprises a polypeptide encoded by a nucleic acid having SEQ ID NO. 12, the method comprising:

(a) contacting the antibody of claim 7 with the sample under conditions permitting complex formation of an antibody-antigen complex; and (b) detecting the presence of any complex so formed.

13. An immunologically reactive polypeptide fragment of the antibody of claim 1 or 3.

14. The antibody of claim 1 or 3, wherein the antibody is a monoclonal antibody.

15. The antibody of claim 1 or 3, wherein said antibody is labelled with a detectable marker.

16. A hybridoma cell line producing the antibody of claim 1 or 3.

* * * * *